US008980185B2

(12) United States Patent
Reichert et al.

(10) Patent No.: US 8,980,185 B2
(45) Date of Patent: Mar. 17, 2015

(54) MICROREACTOR AND METHOD FOR PREPARING A RADIOLABELED COMPLEX OR A BIOMOLECULE CONJUGATE

(75) Inventors: David E. Reichert, St. Louis, MO (US); Paul J. A. Kenis, Champaign, IL (US); Tobias D. Wheeler, Alameda, CA (US); Amit V. Desai, Urbana, IL (US); Dexing Zeng, Pittsburgh, PA (US); Birce C. Önal, Champaign, IL (US)

(73) Assignees: The Board of Trustees of the University of Illinois, Urbana, IL (US); Washington University, St. Louis, MO (US)

( * ) Notice: Subject to any disclaimer, the term of this patent is extended or adjusted under 35 U.S.C. 154(b) by 0 days.

(21) Appl. No.: 13/818,569

(22) PCT Filed: Aug. 25, 2011

(86) PCT No.: PCT/US2011/049057
§ 371 (c)(1),
(2), (4) Date: May 13, 2013

(87) PCT Pub. No.: WO2012/027527
PCT Pub. Date: Mar. 1, 2012

(65) Prior Publication Data
US 2013/0225791 A1    Aug. 29, 2013

Related U.S. Application Data

(60) Provisional application No. 61/377,364, filed on Aug. 26, 2010.

(51) Int. Cl.
G21C 1/00      (2006.01)
C07K 1/13      (2006.01)
C07B 59/00     (2006.01)
B01J 19/00     (2006.01)
C07K 1/107     (2006.01)

(52) U.S. Cl.
CPC . C07K 1/13 (2013.01); C07B 59/00 (2013.01); B01J 19/0093 (2013.01); C07B 59/008 (2013.01); C07K 1/1077 (2013.01)
USPC .......................... 422/159; 424/1.65; 424/1.69

(58) Field of Classification Search
None
See application file for complete search history.

(56) References Cited

U.S. PATENT DOCUMENTS

| | | | |
|---|---|---|---|
| 5,922,604 A * | 7/1999 | Stapleton et al. | 436/46 |
| 6,296,020 B1 | 10/2001 | McNeely et al. | 137/806 |
| 2005/0226776 A1 | 10/2005 | Brady et al. | 422/99 |
| 2007/0017633 A1 | 1/2007 | Tonkovich et al. | 156/300 |
| 2007/0048216 A1 | 3/2007 | Norenberg | 424/1.11 |
| 2007/0217963 A1 | 9/2007 | Elizarov et al. | 422/130 |
| 2008/0224072 A1 * | 9/2008 | Sonnenhol et al. | 250/496.1 |
| 2009/0036668 A1 | 2/2009 | Elizarov et al. | 536/122 |
| 2009/0095635 A1 | 4/2009 | Elizarov et al. | 205/426 |
| 2010/0065512 A1 | 3/2010 | Bjorsvik | 210/766 |

FOREIGN PATENT DOCUMENTS

WO    WO 2007148074 A1 * 12/2007

OTHER PUBLICATIONS

Lee, Chia Yen et al; "Integrated microfluidic systems for cell lysis, mixing/pumping and DNA amplification." J. Micromech. Microeng (2005) 15 p. 1215-1223.*
Stimmel, Julie B. and Kull Jr, Frederick C.; "Samarium-153 and lutetium-177 chelation properties of selected macrocyclic and acyclic ligands." Nuc. Med. Biol. (1998) 25 p. 117-125.*
International Search Report and Written Opinion for International PCT Application No. PCT/US2011/049057, mailing date Mar. 15, 2012, pp. 1-11.
Anderson, Carolyn J. et al., "Copper-64 Radiopharmaceuticals for PET Imaging of Cancer: Advances in Preclinical and Clinical Research," *Cancer Biotherapy and Radiopharmaceuticals*, 24, 4 (2009) pp. 379-393.
Audrain, Hélène, "Positron Emission Tomography (PET) and Microfluidic Devices: A Breakthrough on the Microscale?" *Angewandte Chemie International Edition*, 46 (2007) pp. 1772-1775.
Chen, Xiaoyuan et al., "Integrin $\alpha_v\beta_3$-Targeted Imaging of Lung Cancer," *Neoplasia*, 7, 3 (2005) pp. 271-279.
De Leon-Rodriguez, L.M. et al., "The Synthesis and Chelation Chemistry of DOTA—Peptide Conjugates," *Bioconjugate Chemistry*, 19, 2 (2008) 391-402.
Elizarov, Arkadij M. et al., "Design and Optimization of Coin-Shaped Microreactor Chips for PET Radiopharmaceutical Synthesis," *The Journal of Nuclear Medicine*, 51, 2 (2010) pp. 282-287.
Elizarov, Arkadij M., "Microreactors for radiopharmaceutical synthesis," *Lab on a Chip*, 9 (2009) pp. 1326-1333.
Ferl, G. Z. et al., "Derivation of a Compartmental Model for Quantifying $^{64}$Cu-DOTA-RGD Kinetics in Tumor-Bearing Mice," *The Journal of Nuclear Medicine*, 50, 2 (2009) pp. 250-258.
Gillies, J. M. et al, "Microfluidic reactor for the radiosynthesis of PET radiotracers," *Applied Radiation and Isotopes*, 64 (2006) pp. 325-332.

(Continued)

*Primary Examiner* — James H Alstrum Acevedo
*Assistant Examiner* — Fred Reynolds
(74) *Attorney, Agent, or Firm* — Brinks Gilson & Lione

(57) ABSTRACT

A microreactor for preparing a radiolabeled complex or a biomolecule conjugate comprises a microchannel for fluid flow, where the microchannel comprises a mixing portion comprising one or more passive mixing elements, and a reservoir for incubating a mixed fluid. The reservoir is in fluid communication with the microchannel and is disposed downstream of the mixing portion. A method of preparing a radiolabeled complex includes flowing a radiometal solution comprising a metallic radionuclide through a downstream mixing portion of a microchannel, where the downstream mixing portion includes one or more passive mixing elements, and flowing a ligand solution comprising a bifunctional chelator through the downstream mixing portion. The ligand solution and the radiometal solution are passively mixed while in the downstream mixing portion to initiate a chelation reaction between the metallic radionuclide and the bifunctional chelator. The chelation reaction is completed to form a radiolabeled complex.

6 Claims, 10 Drawing Sheets

(56) References Cited

OTHER PUBLICATIONS

Hicks, Justin W., "Fluorous-Phase Purification of $^{99m}$Tc Radiopharmaceuticals," *Open Access Dissertations and Theses*, Paper 4624, http://digitalcommons.mcmaster.ca/opendissertations/4624, Jan. 2010.

Huhn, C. et al., "Relevance and use of capillary coatings in capillary electrophoresis-mass spectrometry," *Analytical and Bioanalytical Chemistry*, 396 (2010) pp. 297-314.

Kukis, David L. et al., "Optimized Conditions for Chelation of Yttrium-90-DOTA Immunoconjugates," *The Journal of Nuclear Medicine*, 39, 12 (1998) pp. 2105-2110.

Lee, Chung-Cheng et al., "Multistep Synthesis of a Radiolabeled Imaging Probe Using Integrated Microfluidics," *Science*, 310 (2005) pp. 1793-1796.

Leitha, Thomas, "Nuclear Medicine: Proof of Principle for Targeted Drugs in Diagnosis and Therapy," *Current Pharmaceutical Design*, 15 (2009) pp. 1-15.

Lewis, Jason S. et al., "Copper-64-diacetyl-bis(N$^4$-methylthiosemicarbazone): An agent for radiotherapy," *Proceedings of the National Academy of Sciences*, 98, 3 (2001) pp. 1206-1211.

Liu, Shuang, "Bifunctional coupling agents for radiolabeling of biomolecules and target-specific delivery of metallic radionuclides," *Advanced Drug Delivery Reviews*, 60 (2008) pp. 1347-1370.

Liu, Zhaofei et al., "$^{18}$F, $^{64}$Cu, and $^{68}$GA Labeled RGD-Bombesin Heterodimeric Peptides for PET Imaging of Breast Cancer," *Bioconjugate Chemistry*, 20 (2009) pp. 1016-1025.

Lu, Shui-Yu et al., "Syntheses of $^{11}$C- and $^{18}$F-labeled carboxylic esters within a hydrodynamically-driven micro-reactor," *Lab on a Chip*, 4 (2004) pp. 523-525.

Mansur, Elmabruk A. et al., "A State-of-the-Art Review of Mixing in Microfluidic Mixers," *Chinese Journal of Chemical Engineering*, 16, 4 (2008) pp. 503-516.

McDonald, J. Cooper et al., "Poly(dimethylsiloxane) as a Material for Fabricating Microfluidic Devices," *Accounts of Chemical Research*, 35, 7 (2002) pp. 491-499.

Miller, P. W., "Radiolabelling with short-lived PET (positron emission tomography) isotopes using microfluidic reactors," *Journal of Chemical Technology & Biotechnology*, 84 (2009) pp. 309-315.

Oyen, W. J. G. et al., "Targeted therapy in nuclear medicine—current status and future prospects," *Annals of Oncology*, 18, 11 (2007) pp. 1782-1792.

Shokeen, Monica et al., "Molecular Imaging of Cancer with Copper-64 Radiopharmaceuticals and Positron Emission Tomography (PET)," *Accounts of Chemical Research*, 42, 7 (2009) pp. 832-841.

Smith, Suzanne V., "Molecular imaging with copper-64," *Journal of Inorganic Biochemistry*, 98 (2004) 1874-1901.

Stroock, Abraham D. et al., "Chaotic Mixer for Microchannels," *Science*, 295 (2002) pp. 647-651.

Wadas, T. J. et al., "Copper Chelation Chemistry and its Role in Copper Radiopharmaceuticals," *Current Pharmaceutical Design*, 13, 1 (2007) pp. 3-16.

Wadas, Thaddeus J. et al., "Radiolabeling of TETA- and CB-TE2A-conjugated peptides with copper-64," *Nature Protocols*, 1, 6 (2006) 3062-3068.

Wu, Yun et al., "microPET Imaging of Glioma Integrin $\alpha_v\beta_3$ Expression Using $^{64}$Cu-Labeled Tetrameric RGD Peptide," *The Journal of Nuclear Medicine*, 46, 10 (2005) pp. 1707-1718.

\* cited by examiner

MICROREACTOR AND METHOD FOR PREPARING A RADIOLABELED COMPLEX OR A BIOMOLECULE CONJUGATE

RELATED APPLICATIONS

The present patent document is the national stage of International Application No. PCT/US2011/049057, which was filed on Aug. 25, 2011, and which claims the benefit of the filing date under 35 U.S.C. §119(e) of U.S. Provisional Patent Application Ser. No. 61/377,364, which was filed on Aug. 26, 2010, both of which are hereby incorporated by reference in their entirety.

FEDERALLY SPONSORED RESEARCH OR DEVELOPMENT

This invention was made with government support under grant number DE-FG02-08ER64682 from the Department of Energy Office of Biological and Environmental Research and under grant number R24 CA86307 from the National Institutes of Health. The government has certain rights in this invention.

TECHNICAL FIELD

The present disclosure is directed generally to microfluidics technology more particularly to a microfluidic reactor and method for synthesizing radiometal-labeled imaging and therapeutic agents used in nuclear medicine.

BACKGROUND

Nuclear imaging and therapy are vital to several areas of modern medicine, including oncology, cardiology, hematology, and studies of the biodistribution of drugs. These non-invasive techniques rely on the introduction of radioactive agents (radiopharmaceuticals) into the body to detect disease via Positron Emission Tomography (PET) or Single Photon Emission Computed Tomography (SPECT), or to treat disease with ionizing radiation. To minimize the systemic exposure of the body to radiation, and to enhance the specificity and sensitivity of the PET and SPECT imaging techniques, metallic radionuclides (radiometals) are bound to biomolecules (BMs) with bi-functional chelators (BFCs). The BM (e.g., a peptide or an antibody) is selected to have a high affinity for the tissue of interest, to deliver and retain radiation only where it is needed. The BFC is selected to have a high affinity for the radiometal, form a complex with the radiometal that is highly stable in vivo, and possess a functional group that can form a bond with the biomolecule.

Two radionuclides commonly used in nuclear imaging are the positron emitter $^{18}$F (used in PET), and the gamma ray emitter $^{99m}$Tc (used in SPECT). These radionuclides have relatively short half-lives (109 minutes and 6 hours, respectively) that make them favorable for minimizing exposure of the body to radiation, and have decay characteristics that make them optimal for their respective imaging modalities. However, focusing on PET imaging, the relatively short half-life of $^{18}$F and its typical labeling conditions (use of organic solvents) lowers its suitability for use with biomolecules such as antibodies. An alternative radionuclide that has received increasing attention is the positron emitter $^{64}$Cu$^{2+}$. The decay properties of this radiometal allow it to be used both as a PET imaging agent and as a nuclear therapy agent. In addition, its half-life of 12.7 hours and the capability of cyclotron-based production of large quantities with high specific activity (>10,000 mCi/mol) from enriched $^{64}$Ni[3] facilitate the distribution of $^{64}$Cu$^{2+}$ from a central production facility. Further benefits associated with $^{64}$Cu$^{2+}$ include: (1) its well-documented coordination chemistry, redox chemistry, and biochemistry and metabolism in humans, (2) the availability of a variety of azamacrocyclic BFCs that can chelate copper in the 2+ oxidation state with high specificity and stability, and (3) the ability to perform radiolabeling reactions in protein-friendly, aqueous media (as opposed to the organic solvents required for radiolabeling with $^{18}$F), at pH ~7, and at near-physiological temperatures.[9]

Conventional radiolabeling methods for $^{64}$Cu$^{2+}$, and other radiometals, typically require the dilution of small quantities (1-2 mCi≈4 picomoles of $^{64}$Cu$^{2+}$ in ~10 μL is diluted to ~500 μL) for convenient handling and proper mixing, resulting in nanomolar concentrations of the radiometal. This dilution requires a large excess (~100-fold) of the potentially expensive and difficult-to-obtain BFC-BM conjugate to ensure the desired high percentage of bound radionuclide (>90%) within a reasonable time (<1 hour). In turn, the use of large excesses of BFC-BM conjugate necessitates extensive chromatographic purification to remove unlabeled BFC-BMs and to obtain the high specific activities that are desirable for application of the radiopharmaceutical, for example in PET imaging. Chromatographic purification is also potentially required to remove BFC-BM impurities that may bind more strongly or more quickly to the radiometal than the desired BFC-BM conjugate. For instance, if the 100-fold excess of BFC-BM contains 1% impurity, then the molar ratio of impurity to radiometal would be 1:1, potentially leading to the synthesis of unwanted radiometal-ligand complex.

BRIEF SUMMARY

In view of the shortcomings of conventional techniques, the present inventors have developed an improved method and microreactor for producing a radiolabeled complex that may be used as an imaging agent or therapeutic complex in nuclear medicine. The microreactor may also be used to synthesize biomolecule conjugates.

The method includes, according to one aspect, flowing a radiometal solution comprising a metallic radionuclide through a downstream mixing portion of a microchannel, where the downstream mixing portion includes one or more passive mixing elements, and flowing a ligand solution comprising a bifunctional chelator, which may be bound to a biomolecule, through the downstream mixing portion. The ligand solution and the radiometal solution are passively mixed while in the downstream mixing portion, and a chelation reaction between the metallic radionuclide and the bifunctional chelator is initiated. The chelation reaction is completed to form a radiolabeled complex.

The method includes, according to another aspect, flowing a chelator solution and a biomolecule solution through a mixing portion of a microchannel, where the mixing portion includes one or more passive mixing elements, and passively mixing the chelator solution and the biomolecule solution to form a combined solution via a conjugation reaction. A biomolecule conjugate is thereby synthesized.

The microreactor for preparing a radiolabeled complex or a biomolecule conjugate comprises a microchannel for fluid flow, where the microchannel comprises a mixing portion comprising one or more passive mixing elements, and a reservoir for incubating a mixed fluid. The reservoir is in fluid communication with the microchannel and is disposed downstream of the mixing portion.

DETAILED DESCRIPTION

Radiometal-based radiopharmaceuticals, used as imaging and therapeutic agents in nuclear medicine, may include a radiometal that is bound to a targeting biomolecule (BM) using a bifunctional chelator (BFC). Conventional, macroscale radiolabeling methods use an excess of the BFC-BM conjugate (ligand) to achieve high radiolabeling yields. Subsequently, to achieve maximal specific activity (minimal amount of unlabeled ligand), extensive chromatographic purification is required to remove unlabeled ligand, often resulting in longer synthesis times and loss of imaging sensitivity due to radioactive decay.

A microreactor that overcomes the above issues through integration of efficient mixing and heating strategies while working with small volumes of concentrated reagents is described. The general design of the microreactor and its usage are described here, followed by a detailed description of an exemplary microreactor design and experiments carried out using the microreactor. The microreactor may be employed for producing radiolabeled complexes and also for biomolecule conjugation.

1 Introduction to the Microreactor

Figure 1A:
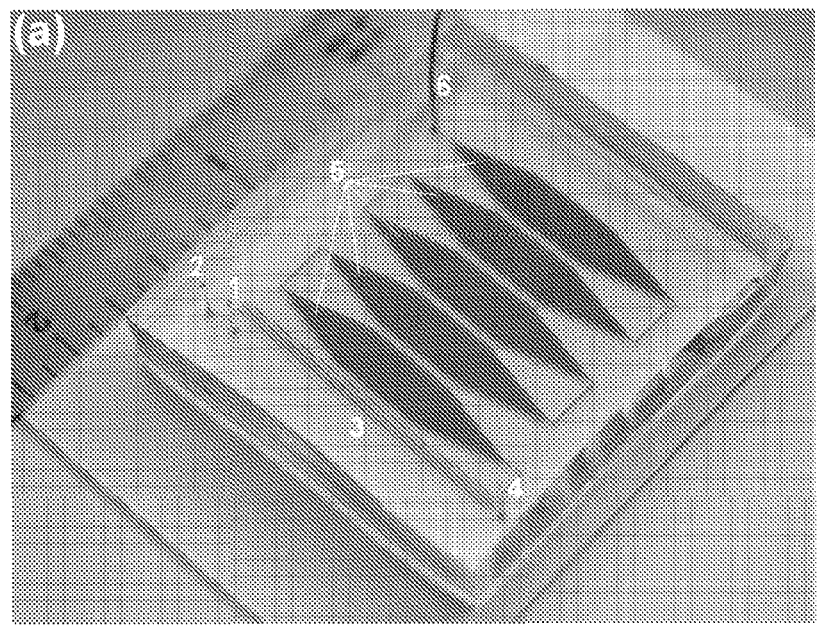
FIG. 1 shows (a) a photograph, and (b) a schematic diagram of an exemplary microreactor where the mixing channels and incubation reservoirs are filled with dye (FIG. 1(a)). In both (a) and (b), 1 is the radiometal inlet, 2 is the buffer inlet, 3 is the serpentine mixing microchannel, 4 is the BFC-BM inlet, 5 are the incubation reservoirs, and 6 is the product outlet. In (b), 3a and 3b are the first and second portions of the microchannel, respectively. The inset in (b) shows an illustration of staggered herringbone grooves defined in the PDMS ceiling of the mixing microchannel. The length, width, and height of the PDMS portion of the exemplary microreactor are ~2"×~1.5"×~0.25". Of course other dimensions are also possible.
Figure 1B:
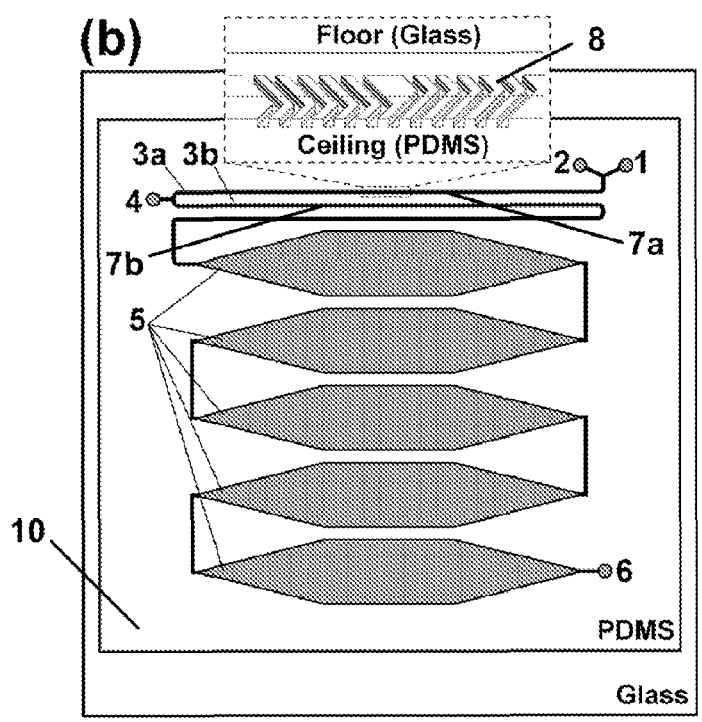

Referring to FIGS. 1(a) and 1(b), the microreactor 10 includes a microchannel 3 for fluid flow, where the microchannel 3 includes a mixing portion comprising one or more passive mixing elements 8. The microreactor 10 also includes at least one reservoir 5 for incubating a mixed fluid. The reservoir 5 is in fluid communication with the microchannel 3 and is disposed downstream of the mixing portion 3.

The mixing portion may be a downstream mixing portion 7b and there may also be an upstream mixing portion 7a of the microchannel 3. A first inlet 1 is positioned upstream of the upstream mixing portion for introduction of a first reagent, a second inlet 2 is positioned upstream of the upstream mixing portion 7a for introduction of a second reagent, and a third inlet 4 is positioned between the upstream mixing portion 7a and the downstream mixing portion 7b for introduction of a third reagent. Referring to FIG. 1(b), the upstream mixing portion 7a is in a first straight portion 3a of the microchannel 3 and the downstream mixing portion 7b is in a second straight portion 3b of the microchannel 3. The first and second straight portions 3a, 3b are thus connected. In the example of FIGS. 1(a) and 1(b), the microchannel 3 defines a serpentine flow path, where the second straight portion 3b is arranged substantially parallel to the first straight portion 3a.

In the example of FIGS. 1(a) and 1(b), the passive mixing elements 8 comprise a series of grooves in a wall of the microchannel 3. This series of grooves defines a staggered herringbone pattern as shown in the inset of FIG. 1(b) and create a chaotic micromixer. Generally speaking, the one or more passive mixing elements 8 may be selected from the group consisting of: multi-lamination micromixers; bifurcation feed micromixers; interdigitated parallel flow micromixers; hydrodynamic focusing micromixers; splitting, recombining and rearranging micromixers; and chaotic micromixers.

The microreactor may include a plurality of the reservoirs 5 arranged in series, as shown in FIGS. 1(a) and 1(b). It is also contemplated that the microreactor may include a plurality of the reservoirs arranged in parallel. The reservoir(s) 5 may have an elongated shape in the direction of fluid flow. For example, again referring to FIGS. 1(a) and 1(b), a longitudinal cross-section of the elongated shape may be a hexagon. According to one embodiment, the reservoirs 5 may hold a total volume of fluid of between about 5 µL and about 1000 µL. The total volume may also be between about 10 µL and 500 µL, or between about 20 µL and 100 µL.

The upstream and downstream mixing portions 7a, 7b of the microchannel 3 may each comprise a length of between about 0.1 cm and about 100 cm. The length may also lie between about 0.5 cm and about 10 cm, or between about 1 cm and about 5 cm. The microchannel may have a total length of between about 0.1 cm and about 100 cm, and the total length may also be between about 0.5 cm and about 50 cm, or between about 1 cm and about 20 cm. The microchannel may have a height of between about 5 microns and about 500 microns and a width of between about 5 microns and about 500 microns. The height may also be between about 25 µm and 300 µm, or between about 50 µm and 200 µm, and the width may also be between about 25 µm and 400 µm, or between about 50 µm and 300 µm.

The first reagent, the second reagent, and the third reagent introduced into the microreactor may be selected from the group consisting of: a precursor radiometal solution comprising a metallic radionuclide, a buffer solution comprising a weak chelating ligand (e.g., ammonium acetate, sodium acetate, ammonium citrate), and a ligand solution comprising a bifunctional chelator. According to one embodiment, the first reagent comprises the radiometal solution, the second reagent comprises the buffer solution, and the third reagent comprises the ligand solution. According to another embodiment, only first and second reagents are introduced to the microchannel at one or more of the inlets. For example, in a conjugation reaction, the first reagent may be a chelator solution comprising a bifunctional chelator and the second reagent may be a biomolecule solution comprising a biomolecule.

Referring again to FIGS. 1(a) and 1(b), a method of preparing a radiolabeled complex includes flowing a radiometal solution comprising a metallic radionuclide through a downstream mixing portion 7b of a microchannel 3, where the downstream mixing portion 7b includes one or more passive mixing elements 8. A ligand solution comprising a bifunctional chelator is also flowed through the downstream mixing portion 7b, and the ligand solution and the radiometal solution are passively mixed while in the downstream mixing portion 7b to form a mixed solution and to initiate a chelation reaction between the metallic radionuclide and the bifunctional chelator. The chelation reaction is completed to form a radiolabeled complex.

The method may further comprise, prior to flowing the radiometal solution through the downstream mixing portion 7b of the microchannel 3, flowing a buffer solution and a precursor radiometal solution comprising the metallic radionuclide through an upstream mixing portion 7a of the microchannel 3, where the upstream mixing portion 7a includes one or more passive mixing elements 8. The buffer solution and the precursor radiometal solution are passively mixed while in the upstream mixing portion 7a to form the radiometal solution.

Completing the chelation reaction may entail halting the flow of each solution and incubating the mixed solution for an incubation time sufficient to form the radiolabeled complex. Referring again to FIGS. 1(a) and 1(b), the incubation may be carried out in a microfluidic reservoir 5 in fluid communication with the microchannel 3 and disposed downstream of the downstream mixing portion 7b. The method may further include flowing a fluid into the microfluidic reservoir after the incubation to force the mixed solution through a reservoir outlet 6. The incubating may be carried out at a temperature between about 0° C. and about 100° C. The temperature may also be between about 20° C. and about 60° C. The incubation time is typically greater than 1 minute, and may be from about 5 minutes to about 20 minutes.

The method may further or alternatively include forming a biomolecule conjugate. A chelator solution comprising molecules with coordination sites for radiometal (e.g., $^{64}$Cu, $^{68}$Ga) or signal-contrasting molecule binding (e.g., optical dyes) and a biomolecule solution comprising cell or tissue targeting agents (e.g., tumor targeting molecules) may be flowed through a mixing portion of a "second" microchannel separate from the microchannel 3 described above, where the mixing portion of the second microchannel includes one or more passive mixing elements. The chelator solution and the biomolecule solution are passively mixed to form a combined solution via a conjugation reaction, and a biomolecule conjugate is thus formed. The combined solution may be a ligand solution that is used in the chelation reaction described above to form a radiolabeled complex; in this case, the second microchannel may be in fluid communication with the inlet 4 to the microchannel 3. Alternatively, the conjugation process may be employed to form biomolecule conjugates for other applications, and the second microchannel may be part of a microreactor that is not employed for preparing radiolabeled complexes.

The second microchannel and the one or more passive mixing elements employed in a conjugation reaction such as that described above may have any of the features and dimensions set forth above with respect to the microchannel 3 (the "first" microchannel) and the passive mixing elements 8.

The method may further comprise, prior to flowing the chelator solution and the biomolecule solution through the second microchannel, immobilizing a Cu (I) catalyst on one or more walls of the second microchannel and a second reservoir. As discussed in greater detail below, immobilization of the Cu (I) catalyst may entail: attaching silane acrylate to the wall; attaching a copper (I) stabilizing molecule to the silane acrylate to form a pre-treated wall; and adding a Cu (I) stock solution to the pre-treated wall.

In either the radiolabeling or the conjugation process, the flowing of each of the solutions may occur at a flow rate between about 0.1 µL/min and about 5 mL/min. The flow rate may also be between about 1 µL/min and about 500 µL/min, or between about 10 µL/min and about 100 µL/min. The volume of each of the solutions may be about 1000 µL or less. For example, the volume may be between about 1 µL and about 100 µL, or between about 10 µL and about 50 µL.

The metallic radionuclide employed for radiolabeling may be selected from the group consisting of: 55Co, 60Cu, 61Cu, 64Cu, 67Cu, 66Ga, 67Ga, 68Ga, 110mIn, 111In, 177Lu, 52Mn, 186Re, 188Re, 44Sc, 94mTc, 99mTc, 48V, 86Y, 90Y, and 89Zr. The metallic radionuclide may have a concentration in the radiometal solution of about 10 mM or less. The concentration may also be at least about 50 µM, or at least about 1 mM. According to one embodiment, the molar ratio of the metallic radionuclide to the bifunctional chelator may be about 1:1.

The bifunctional chelator may be a polyaza macrocycle, such as a tetraazacycloalkane, which may be selected from the group consisting of 1,4,7,10-tetraazacyclododecane-1,4,7,10-tetraacetic acid (DOTA) and derivatives thereof, triethylenetetramine (TETA) and derivatives thereof, 1,4,7-triazacyclononane-1,4,7-triacetic acid (NOTA) and derivatives thereof, deferoxamine (desferral), diethylene triamine pentaacetic acid (DTPA) and derivatives thereof, CHX-DTPA and derivatives thereof, CB-TE2A, and sarcophagine (SarAr). The chelator may be conjugated to a targeting biomolecule The targeting biomolecule may be selected from the group consisting of ibritumomab, tositumomab, epratuzumab, a carcinoembryonic antigen, a tumor associated glycoprotein 72 antigen (Anti-TAG-72), an Anti-A33, an Anti-MUC-1, an Anti-gp 38 (folate receptor), an anti-G250 (carbonic anhydrase IX), somatostatin, gastrin, bombesin, glucagon-like peptide-1 (GLP-1), Arginine-Glycine-Aspartic acid (RGD), neuropeptide-Y, stromal cell-derived factor-1 (SDF-1), annexin, and hepcidin and cyclo(Arg-Gly-Asp-DPhe-Lys).

The radiolabeled complex may be obtained at a yield of at least about 20%. For example, the yield may be at least about 50% or at least about 80%.

As a model reaction, 1,4,7,10-tetraazacyclododecane-1,4,7,10-tetraacetic acid (DOTA) conjugated to the peptide cyclo (Arg-Gly-Asp-DPhe-Lys) is radiolabeled with $^{64}Cu^{2+}$. The microreactor (made from polydimethylsiloxane and glass) can withstand 260 mCi of activity over 720 hours. Additionally, once the negatively-charged glass surface of the microreactor is saturated with injected positive ions, minimal retention of the $^{64}Cu^{2+}$ (<5%) occurs for subsequent injections. A direct comparison between the radiolabeling yields obtained using the microreactor and conventional radiolabeling methods shows that improved mixing and heat transfer in the microreactor leads to higher yields for identical reaction conditions. Most importantly, by using small volumes (~10 µL) of concentrated solutions of reagents (>50 µM), yields of over 90% are obtainable in the microreactor when using a 1:1 stoichiometry of radiometal to BFC-BM. These high yields obviate the need for a chromatographic purification process to remove unlabeled ligand. The results reported here demonstrate the potential of microreactor technology to improve the production of patient-tailored doses of radiometal-based radiopharmaceuticals in the clinic.

The remainder of this disclosure is arranged as follows: after a discussion of the design of the microreactor and of the motivations behind the incorporation of its features, the results of an investigation into the compatibility of $^{64}Cu^{2+}$ with PDMS and glass, the materials used in the construction of the microreactor, are described. Also presented are results of an evaluation of the performance of the microreactor conducted using a model radiolabeling reaction: the chelation of $^{64}Cu^{2+}$ by 1,4,7,10-tetraazacyclododecane-1,4,7,10-tetraacetic acid (DOTA) conjugated to the peptide cyclo(Arg-Gly-Asp-DPhe-Lys) (cyclo(RGDfK)). The resulting radiotracer has potential applications in the detection of cancer via PET. In this evaluation, the effects of incubation time, temperature, and synthesis method (micro-scale vs. macro-scale) on the radiolabeling yield for 1:1 stoichiometric ratios of $^{64}Cu^{2+}$ to DOTA-cyclo(RGDfK) are examined. Finally, a range of reagent concentrations is established at which high radiolabeling yields are obtainable (>90%) and for which chromatographic separation of unlabeled BFC-BMs is no longer necessary for the clinical production of radiopharmaceuticals.

2 Design and Testing 2.1 Design of the Microreactor

Presented here is an exemplary PDMS-based, microfluidic reactor for labeling BFC-BMs with radiometals. Referring to FIGS. 1(a) and 1(b), the microreactor includes three key elements: (1) a serpentine microchannel for mixing, in which staggered herringbone grooves are defined using soft lithography; (2) a series of reservoirs for the incubation of the radiometal-ligand mixture; and (3) a thin-film heater for heating the mixture.

Serpentine mixing channel: The microreactor incorporates a passive mixer (Stroock et al., Science, 2002, 295 (647-651)) to minimize diffusive limitations to the overall rate of the radiolabeling reaction. Generally, in the laminar, low Reynolds number flow that occurs at the microscale, when two streams of reagents are brought in contact, a depletion zone forms as a result of the consumption of the reagents at the interface between the two streams. This depletion zone grows in the transverse direction as the streams flow axially along the channel. As a result, the reagents must diffuse across increasingly longer distances in order for the reaction to proceed. The small scale of microfluidic systems renders them less susceptible to the growth of large depletion zones than macro-scale systems (the distance for diffusion, $\Delta r$ [m], is ultimately limited to half the width of a microchannel, $w/2 \sim 100$ µm. However, the time scale for diffusion across the channel in microfluidic systems, $T_D = \Delta r^2 / D$, where D [$m^2 s^{-1}$] is the diffusivity of the reagent, can still be significant (on the order of minutes), particularly for large molecules that have low diffusivities in water (D<$10^{-11}$ $m^2 s^{-1}$), such as proteins and antibodies, compared to the time scale of the reaction, $T_R = 1/kC_0^n$, where k [$M^{-n}s^{-1}$] is the reaction rate constant, $C_0$ [M] is the initial concentration of the reagent, and n is the order of the reaction. Thus, depletion zones can impose diffusive mass transport limitations on the rate of a reaction that occurs in a microchannel and should be avoided, particularly for high-throughput reactions with fast kinetics.

Passive mixing of reagents, generated by staggered herringbone grooves, is introduced to further reduce, and potentially eliminate entirely, the limitation to reaction kinetics caused by depletion zones. The staggered herringbone grooves in the mixing channel induce chaotic stirring in the cross-section of the flow that stretches and folds the interface between the co-flowing, laminar streams. This stretching and folding reduces the maximum distance, $\Delta r$, that the solutes in the initially separate streams must diffuse in order to form a homogeneous mixture and to react, resulting in smaller depletion zones, and thus a reduced potential for diffusive mass transport limitations on the rate of reaction. The maximum diffusive distance for chaotic stirring can be approximated by, $\Delta r = w/2 \exp(-\Delta y/\lambda)$, where w [m] is the width of the microchannel, $\Delta y$ [m] is the distance traveled along the axis of the microchannel, and $\lambda$ [m] is a characteristic length determined by the geometry of the trajectories of the chaotic stirring. Based on this equation and the estimated value of $\lambda \sim 2$ mm for the chaotic stirring induced by the grooves, once the two streams have reached the end of a 3 cm-long, grooved microchannel, $\Delta r$ will have decreased by roughly six orders of magnitude, yielding a reduction in $T_D$ of 12 orders of magnitude. This drastic reduction in mixing time eliminates any mass transport limitations to the reaction rates, as is desired for the radiometal labeling chemistries pursued here. Furthermore, the relatively short length of the mixing channel afforded by using chaotic stirring, as opposed to the longer channel lengths that would be required when relying solely on diffusion to mix, enables the use of high flow rates (>500 µL min$^{-1}$), without developing prohibitively large pressure drops. This aspect is useful for high-throughput radiolabeling, when chelation rates are fast.

Reservoirs and Heater: For the case when chelation rates are slow, the microreactor incorporates a series of reservoirs and a thin film heater. The high degree of homogeneity of the reagent mixture that is accomplished through the use of staggered herringbone grooves for mixing allows for the accumulation of clinically relevant volumes of the mixture (up to 50 µL per run) in the reservoirs, without provoking mass transport limitations to the rate of the radiolabeling reaction. If regions of incomplete mixing were present, these regions, and the depletion zones that develop within them, would be magnified through the expansion of the microchannel into the wider reservoir, and diffusive mass transport limitations would be exacerbated. In the microreactor presented here, the well-mixed solution of reagents can be incubated for arbitrary periods of time at elevated temperatures to achieve high yields, and then flushed quickly from the microreactor for use.

Figures 2A, 2B:
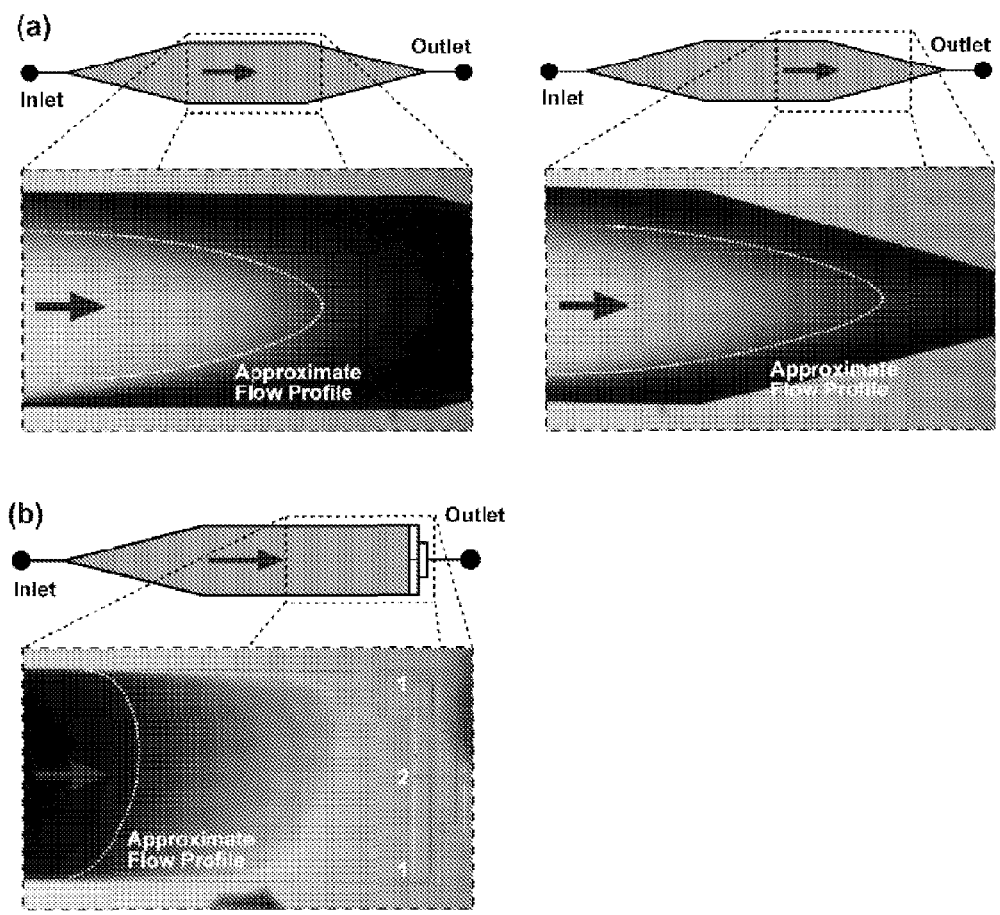
FIGS. 2(a)-2(b) show (a) flow profile in an exemplary hexagonal reservoir and (b) flow profile in an exemplary reservoir with a three-channel manifold. In (a) and (b), the approximate flow profile is indicated with a dashed white line, and the arrows indicate the direction of flow. In (a), slow-moving liquid at the edge of the reservoir has a higher residence time than fast-moving liquid at the center of the reservoir. Additional liquid may be injected to fully flush out the contents of the reservoir. This additional liquid results in dilution of the contents of the reservoir. Furthermore, additional elongation of the flow profile can be seen in the triangular section near the outlet. In (b), the flow profile is significantly flatter, providing a more uniform residence time across the width of the reservoir. Less additional liquid may be injected to fully flush out the contents of the reservoir, resulting in less dilution. In this example, the ratio of the width of the outer exit channels (labeled 1 in FIG. 2(b)) to the central exit channel (labeled 2 in FIG. 2(b)) is 4:1.

The reservoirs can have any of a variety of shapes, including the elongated hexagonal shape shown in FIG. 1(a)-(b), or a triangular entrance region, a rectangular central section and a multi-channel manifold at the exit, as shown in FIG. 2(b). Viscous drag at the walls of the hexagonal reservoirs results in the elongation of the flow profile, as is shown in FIG. 2(a). The consequence of this elongation is that, while the mixture near the center of a reservoir can be easily flushed out, using a single reservoir-volume of flushing solution, the mixture near the edge of the reservoir may be left behind and may require additional flushing to eject. A 3-channel manifold configuration reduces the volume of additional flushing solution required to fully flush the incubated mixture from the reservoir by increasing the relative flow rate at the edge of the reservoir and thereby reducing the elongation of the parabolic profile of flow through the reservoir, as shown in FIG. 2(b).

In an experiment, water was injected into a hexagonal reservoir filled with ink (flow rate=20 µL/min). The height of the reservoir was 100 µm. The central, rectangular portion of the reservoir was 5 mm wide and 10 mm long, and both of the triangular sections on either side of the rectangular section were 5 mm wide and 10 mm long. The results are shown in FIG. 2(a).

In another experiment, ink was injected into a reservoir filled with water (flow rate=20 µL/min) and including a 3-channel manifold at the outlet end. The height of the reservoir was 100 µm. The rectangular section toward the outlet was 5 mm wide and 20 mm long. The triangular section to the left of the rectangular section was 5 mm wide and 10 mm long. The width of outlet channels 1 and 2 were 200 µm and the width of outlet channel 3 was 50 µm. The results are shown in FIG. 2(b). The ratio of the widths of the exit channels of the reservoir can be optimized to further flatten the flow profile.

The simple features of the microreactor discussed above provide a great deal of flexibility for radiolabeling BFC-BMs. The microreactor can perform both high-throughput, continuous flow radiolabeling for fast chelation rates, and semi-batch, incubated radiolabeling for slow chelation rates. In addition, the simplicity of the design (i.e., the lack of extensive networks of microchannels and of valves and their required ancillary equipment) is beneficial for its envisioned use in the clinic as an inexpensive, disposable microreactor for the custom, on-demand synthesis of radiopharmaceuticals.

2.2 Testing of the Microreactor

The microreactor was validated by labeling a BFC-BM conjugate with $^{64}Cu^{2+}$. The BFC-BM conjugate included the bifunctional chelator 1,4,7,10-tetraazacyclododecane-1,4,7,10-tetraacetic acid (DOTA), and the peptide cyclo(Arg-Gly-Asp-DPhe-Lys) (cyclo(RGDfK)). This peptide targets $\alpha_v\beta_3$ integrin, a receptor that is up-regulated on the surface of cells undergoing angiogenesis. The high occurrence of angiogenesis in tumors results in a higher concentration of $\alpha_v\beta_3$ integrin, and therefore a higher concentration of bound, radiolabeled RGD, in contrast with the surrounding, healthy tissue. Radiolabeled RGD-based imaging agents are promising candidates for the imaging of tumors via PET.

Figures 3A, 3B:
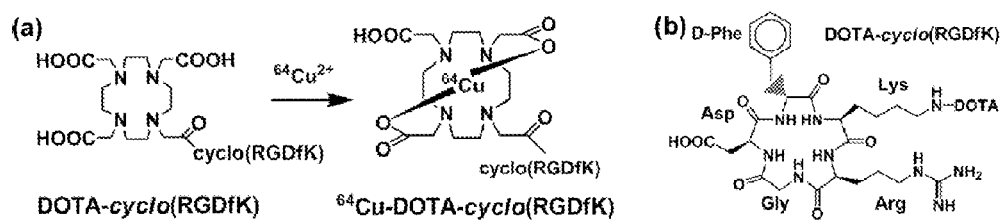
FIG. 3(a) illustrates the reaction scheme of the chelation of $^{64}Cu^{2+}$ by DOTA-cyclo(RGDfK). Of the four pendant arms of DOTA, two are used in chelation of the radiometal and one is used to conjugate the biomolecule cyclo(RGDfK).
FIG. 3(b) shows the structure of cyclo(RGDfK) and the position at which DOTA is conjugated to the biomolecule.

The radiolabeling reaction, summarized in FIG. 3(a), includes three steps: (1) the addition of $^{64}Cu^{2+}$ in 0.1N HCl (the normal state of the radiometal as it is received the cyclotron) to 10 mM ammonium acetate (NH$_4$OAc) (pH=6.8) to form $^{64}Cu(OAc)_2$ through ligand exchange; (2) the addition of DOTA-cyclo(RGDfK) (see FIG. 3(b)) in 10 mM NH$_4$OAc (pH=6.8) to the $^{64}Cu(OAc)_2$ mixture to form $^{64}Cu$-DOTA-cyc/o(RGDfK) through chelation; (3) the incubation of the $^{64}Cu$-DOTA-cyc/o(RGDfK) mixture at room or elevated temperature to drive the chelation reaction to completion. The two-step combination of reagents is performed in the serpentine mixing channel of the microreactor, with radiometal and buffer solutions mixing in the first leg of the channel (3a in FIG. 1(b)) and ligand and radiometal-buffer solutions mixing in the second leg of the channel (3b in FIG. 1(b)).

After passing through the mixing channels, the reagents flow into the reservoirs, where they are incubated at room or elevated temperatures for a certain period of time. This incubation step is important, as the chelation of $^{64}Cu^{2+}$ by DOTA-cyclo(RGDfK) likely involves the rate-limiting rearrangement of a di- or mono-protonated intermediate before chelation is complete, as is the case for the formation of lanthanide complexes (Ln$^{3+}$) with DOTA-peptide conjugates.

3 Materials and Methods

3.1 Chemicals

RTV 615 poly(dimethyl siloxane) (PDMS) was obtained from General Electric Company (Waterford, N.Y.). SU-8 2050 was obtained from MicroChem Corporation (Newton, Mass.). (Tridecafluoro-1,1,2,2-tetrahydrooctyl) trichlorosilane was obtained from Gelest, Inc. (Morrisville, Pa.). Cyclo (RGDfK) was purchased from Peptides International, Inc. (Louisville, Ky.). 1,4,7,10-Tetraazacyclodo-decane-1,4,7,10-tetraacetic acid mono (N-hydroxysuccinimide ester) (DOTA-NHS-ester) was purchased from Macrocyclics (Dallas, Tex.). $^{64}Cu^{2+}$ in 0.1 M HCl was produced at Washington University School of Medicine, and obtained through the Radionuclide Resource for Cancer Applications. De-ionized water (DI-$H_2O$) was produced using a Millipore Milli-Q water system. All other chemicals and solvents were purchased from Sigma-Aldrich (St. Louis, Mo.).

3.2 Equipment

Three sets of female ¼-28 to female Luer lock adaptors with ferrules and nuts, PEEK tubing of 1/16" OD and 0.01" ID, and a NanoTight kit with 1/16"×0.027" FEP sleeves, obtained from Upchurch Scientific (Oak Harbor, Wash.) and Microbore PTFE tubing (0.012" ID×0.030" OD) obtained from Cole-Parmer (Vernon Hills, Ill.) were assembled to connect syringes to the microreactor. The 75 mm×50 mm×1 mm glass slide, used to assemble the microreactor, and the Fisher Vortex Genie 2 were obtained from Fisher Scientific (Pittsburgh, Pa.). A test grade, 3" silicon wafer, obtained from University Wafer (South Boston, Mass.) was used to fabricate the SU-8 mold for the microreactor. Three microliter flow modular pump components, which included a syringe pump, a pump driver circuit, and a power supply, were obtained from Harvard Apparatus (Holliston, Mass.). The Kapton-insulated, 2"×2", thin film heater, the Omega CN740 temperature controller, and an Omega SA 1-RTD probe were obtained from Omega Engineering (Stamford, Conn.). The Harrick plasma cleaner was obtained from Harrick Plasma (Ithaca, N.Y.). Eppendorf tubes were obtained from MIDSCI, Inc. (St. Louis, Mo.). The BioScan AR-2000 radio-TLC plate reader was purchased from Bioscan, Inc. (Washington, D.C.). The Thermomixer was obtained from Eppendorf North America (Hauppauge, N.Y.). Radio-TLC plates were obtained from Whatman Thin Layer Chromatography (Piscataway, N.J.). Gas-tight, microliter syringes were obtained from Hamilton Co. (Reno, Nev.). The Waters HPLC systems used in the purification of DOTA-cyclo(RGDfK) was obtained from Waters Corporation (Milford, Mass.). The Capintec CRC-712M radioisotope dose calibrator used to measure activities for retention experiments was obtained from Capintec, Inc. (Ramsey, N.J.).

3.3 Synthesis and Purification of DOTA-cyclo(RGDfK)

DOTA-cyclo(RGDfK) was prepared by reacting a solution of 6.03 mg cyclo(RGDfK) and 14.0 µL triethylamine (10 eqv.) in 1.0 mL dimethylformamide (DMF) with 8.38 mg DOTA-NHS (1.1 eqv). After stirring for 3 hours at room temperature, 3 mL of DI-$H_2O$ were added and stirred for another 30 minutes to hydrolyze the excess DOTA-NHS ester. The crude DOTA-cyclo(RGDfK) was then purified on a Waters HPLC system using an Alltech Econosil C18 semi-preparative column (10 µm, 4.6 mm×250 mm) with a mobile phase of 15 v % acetonitrile and 85 v % de-ionized water with 0.1 v % trifluoroacetic acid (TFA), at a flow rate of 3.0 mL minute$^{-1}$. Under these conditions, the DOTA-cyclo(RGDfK) eluted at 13.5 minutes. The identity and purity of the purified DOTA-cyclo(RGDfK) peptide was confirmed by LC-MS using an Alltech Econosil C18 analytical column (10 µm, 4.6 mm×250 mm). The analysis was performed using the following gradient of 0.1 v % TFA in de-ionized water (A) and acetonitrile (B) with a flow rate of 1.0 mL minute$^{-1}$: 0-5 minutes: 100% A; 20 minutes: 60% A, 40% B; 28-33 minutes: 10% A, 90% B; 34-40 minutes: 100% A.

3.4 Fabrication of the Microreactor

An exemplary microreactor was fabricated using SU-8-based soft-lithography techniques for PDMS. The dimensions of the features shown in FIG. 1 are as follows: serpentine microchannel (100 µm high, 200 µm wide, 10.7 cm long), five hexagonal reservoirs (100 µm high, 5 mm wide, 3 cm long), microchannels between reservoirs (100 µm high, 200 µm wide, 7.2 mm long). The total volume of all five reservoirs is 50 microliters. The staggered herringbone grooves in the mixing channels (see expanded view in FIG. 1b) were designed to have the same geometry as those developed by Stroock et al. An SU-8 mold of the features was fabricated as follows: (1) negative images of the microchannels, inlets, outlets, and reservoirs were printed on one transparency film and the those of the grooves were printed on a second transparency film, using a 5080 dpi printer; (2) the pattern of the microchannels, inlets, outlets, and reservoirs was transferred from the first transparency to a 100 µm-thick layer of SU-8 2050 spun onto a silicon wafer, via photolithography; (3) the pattern of the grooves was transferred from the second transparency to a second, 50 µm-thick layer of SU-8 2050 that was spun over the first layer, following an alignment step so as to define the grooves directly above the mixing channel; (4) unexposed SU-8 was dissolved using propylene glycol methyl ether acetate (PGMEA), and the exposed silicon surface was passivated via vapor deposition of (tridecafluoro-1,1,2,2-tetrahydrooctyl) trichlorosilane, under vacuum. PDMS (10:1 ratio of precursor to curing agent) was then poured over the SU-8 mold and cured at 60° C. for 2+ hours. The cured PDMS was removed from the mold, inlet and outlet holes were punched, and the PDMS was bonded to a 75 mm×50 mm×1 mm glass slide, after 1 minute plasma treatment of both components with a Harrick Plasma Cleaner (RF level: Hi, Pressure: 500-1000 mTorr), followed by baking at 60° C. for 12 hours.

3.5 Operation of the Microreactor

The microreactor may be operated in semi-batch mode or in continuous flow mode. Upon entering the microreactor through inlets 1 and 2, respectively, a radiometal solution and a buffer solution flowed through the mixing channel (3a, 3b in FIG. 1(b)). As the two solutions flowed along the microchannel, they were mixed by the chaotic advection induced by the geometry of the grooves. Once the buffer and radiometal solutions reached the end of the first mixing channel, the ligand (BFC-BM) solution was pumped into the microreactor through inlet 4 and mixed with the radiometal-buffer mixture in a second mixing microchannel with staggered herringbone grooves defined in the ceiling. The mixed reagents then filled a series of five hexagonal reservoirs (5 in FIGS. 1(a),(b)), after which the flow was stopped and the mixture was heated to the desired temperature and allowed to react for a specified incubation time. After this incubation time, the buffer solution was pumped into the microreactor to flush out the product, through the outlet (6 in FIGS. 1(a),(b)), for collection. Other fluids (liquids or gases) may be employed in lieu of the buffer solution to flush out the product.

Figure 4:
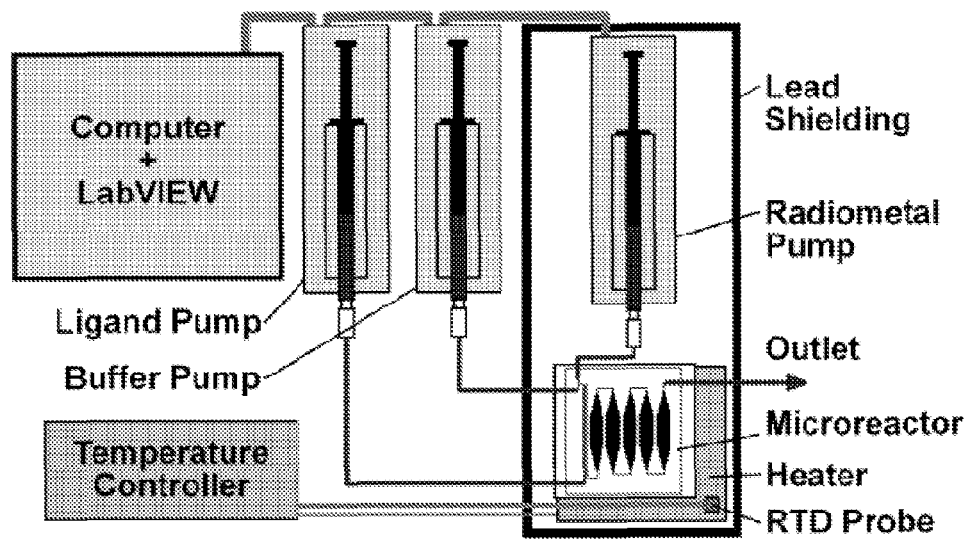
FIG. 4 shows a schematic diagram of an exemplary radiolabeling system. Three LabVIEW-controlled syringe pumps drive the flow of the BFC-BM (ligand), buffer, radiometal solutions into the microreactor. A thin-film heater, controlled using a temperature controller and a resistance temperature detector (RTD) probe affixed to the heater, sets the incubation temperature. Lead shielding surround the microreactor and radiometal pump when operating with radioactive reagents.

A schematic diagram of the system used to operate the microreactor is shown in FIG. 4. The flow of each reagent stream, radiometal, buffer, and ligand, into the microreactor was driven by syringe pumps that were controlled by a LabVIEW virtual instrument (VI). Communication between the VI and the syringe pump drivers was facilitated by a serial connection. The VI was used to set the individual flow rates and regulate the timing of the pumps, with inputs for controlling the incubation time, the total flow rate, the desired volume of product (the maximum being the total volume of the reservoirs, ~50 μL), and the stoichiometric molar ratios of buffer-to-radiometal and ligand-to-radiometal. For radiolabeling at elevated temperatures, a thin-film heater, placed in contact with the glass surface of the microreactor, was used to heat the microreactor, and a temperature controller and resistance temperature detector (RTD) probe were used to maintain the temperature within ±1° C. of the desired temperature set-point. The radiometal syringe pump, heater, and microreactor were shielded on four sides and below with 2" of lead shielding. The radiometal syringe was fitted with a 7.5 cm length of PEEK tubing connected to an Upchurch Luer lock fitting. The PDMS microreactor was fit with a 10 cm length of PTFE tubing connected to an Upchurch NanoTite fitting. The syringe and PEEK "needle" were inserted into the fitting and tightened.

3.6 Measurement of the Retention of $^{64}Cu^{2+}$

A 3 cm-long, 200 μm-wide, 100 μm-tall microchannel with staggered herringbone grooves, fabricated from PDMS and glass and with a volume of ~0.6 μL, was used for these experiments. Prior to use, the microchannel was cleaned with 50 μL of 1N nitric acid to remove trace metals, and flushed with 5 mL of 10 mM NH4OAc buffer solution.

Pre-treatment with Cu2+/Na+: 50 μL of a 10 mM CuCl2/NaCl solution was injected into the microchannel and allowed to sit for 30 minutes. The microchannel was then flushed with 5 mL of 10 mM NH4OAc buffer solution (pH=6.8).

Retention measurement: 30 μL of no carrier-added (only radioactive) 64Cu2+ in 10 mM NH4OAc buffer solution (pH=6.80) was injected into the microchannel. After 10 minutes, the 64Cu2+ solution was displaced from the microchannel by 200 μL of air, via syringe. The microchannel was then flushed with 200 μL of 10 mM NH4OAc buffer. The percent of injected activity retained in the microchannel was calculated from the known activity of the injected solution, and the difference between the activity left behind in the microchannel after flushing and the initial activity of the microchannel measured before the 64Cu2+ solution was injected, all measured with the Capintec radioisotope dose calibrator.

3.7 Radiolabeling of DOTA-cyclo(RGDfK)

Stock solutions of carrier-added $^{64}Cu^{2+}$ were prepared by first diluting the solution obtained from the cyclotron (20 mCi $^{64}Cu^{2+}$ in 0.1M HCl) with 10 mM NH$_4$OAc (pH=6.8) to give a specific activity of 1 mCi μL$^{-1}$. The various copper solutions were then prepared from this original stock solution. In order to prepare a 200 μM carrier-added $^{64}Cu^{2+}$ solution, 20 μL of the 1 mCi μL$^{-1}$ $^{64}Cu^{2+}$ solution was mixed with 20 μL of 10 mM non-radioactive copper solution and 960 μL of 10 mM NH$_4$OAc (pH=6.8). The different concentrations of carrier-added $^{64}Cu^{2+}$ solutions listed in sections 3.7.1 and 3.7.2 were obtained by the dilution of the above 200 μM carrier-added $^{64}Cu^{2+}$ solution with 10 mM NH$_4$OAc.

Stock solutions of 10 mM DOTA-cyclo(RGDfK) were prepared by first dissolving 10.0 mg of purified DOTA-cyclo(RGDfK) (section 3.3) in 100 μL of a mixture of 10 mM NH$_4$OAc (pH=6.8) and acetonitrile (MeCN) (50:50 v %), and then diluting these solutions with 10 mM NH$_4$OAc (pH=6.8) to give final concentrations of 200, 100, 40, and 2 μM DOTA-cyclo(RGDfK).

3.7.1 Conventional Radiolabeling Procedures

Conventional radiolabeling was performed using two methods: (1) mixing, incubation and heating of a total volume of 10.5 μL of solution with a Thermomixer, and (2) mixing of a total volume of 105 μL of solution using a vortexer, followed by continued mixing, incubation and heating with a Thermomixer. For method (1), 3.0 μL of 100 μM DOTA-cyclo(RGDfK) solution was first added to 1.5 μL of 10 mM NH$_4$OAc (pH=6.8) in a 1.6 mL Eppendorf tube. Then, 6.0 μL of 50 μM $^{64}Cu^{2+}$ solution was added to the mixture, and the Eppendorf tube was placed in the Thermomixer and incubated for 12 minutes at a temperature of 23, 37 or 47° C. For method (2), 30 μL of 100 μM DOTA-cyclo(RGDfK) solution was first added to 15 μL of 10 mM NH$_4$OAc (pH=6.8) in a 1.6 mL Eppendorf tube. Then, 60 μL of 50 μM $^{64}Cu^{2+}$ solution was added to the mixture, the mixture was vortexed for 10 seconds, and the Eppendorf tube was placed in the Thermomixer and incubated for 12 minutes at a temperature of 23, 37 or 47° C. The final concentration of $^{64}Cu^{2+}$ and DOTA-cyclo(RGDfK) was 28.6 μM in both methods. Following the incubation period, the extent of reaction was determined as described in section 3.7.3.

3.7.2 Microreactor Radiolabeling Procedure

The general mode of operation of an exemplary microreactor is described in section 3.5. For the radiolabeling experiments summarized in FIG. 5(a) (effect of residence time on extent of reaction) and FIG. 5(b) (effect of mixing method and temperature on extent of reaction), the following solutions were used: (1) 50 μM carrier-added $^{64}Cu^{2+}$ solution, (2) 100 μM DOTA-cyclo(RGDfK) stock solution, and (3) 10 mM NH$_4$OAc (pH=6.8) buffer. Using the LabVIEW interface, the pumps were programmed to combine the radiometal (1), ligand (2), and buffer (3) solutions with the same volumetric ratios as those used for the conventional radiolabeling procedure, giving a ligand-to-metal molar ratio of 1:1 and a final concentration of $^{64}Cu^{2+}$ and DOTA-cyclo(RGDfK) of 28.6 μM. The total flow rate was set to 50 μL minute$^{-1}$, the total volume was set to 20 μL (an additional 30 μL of buffer was pumped into the microreactor to fill all the reservoirs). For the experiments in FIG. 5(a), the temperature was set to 37° C., and the incubation time was set to 5, 10, and 20 minutes (resulting in total residence times, $t_{RES}$=7, 12, and 22 minutes: e.g., 1 minute for filling+10 minutes for incubation+1 minute for flushing). For the experiments in FIG. 5(b), the incubation time was set to 10 minutes ($t_{RES}$=12 minutes), and the temperature was set to 23, 37 and 47° C. After the collection of product, the extent of reaction was determined as described in section 3.7.3.

Figure 6:
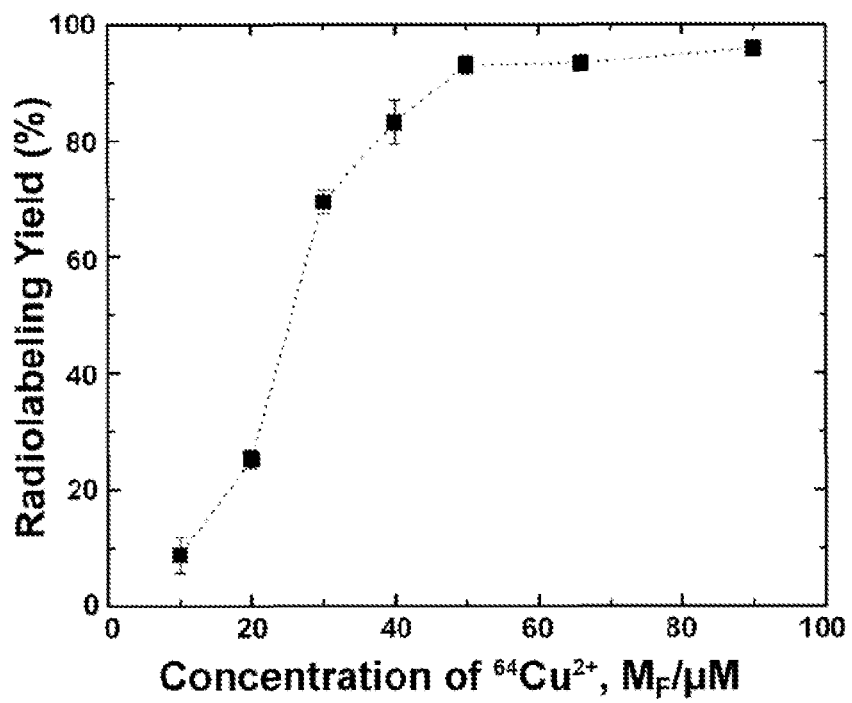
FIG. 6 shows radiolabeling yield as a function of the final concentration of $^{64}Cu^{2+}$, $M_F$, using a 1:1 stoichiometric ratio of $^{64}Cu^{2+}$ to DOTA-cyclo(RGDfK). Error bars represent standard deviation in the extent of reaction for three experiments ($t_{RES}=12$ minutes, T=37° C.), using radiometal solutions made from the same batch of $^{64}Cu^{2+}$. Lines between points are guides for the eye.

For the radiolabeling experiments summarized in FIG. 6 (effect of concentration on extent of reaction), combinations of stock solutions and buffer-to-metal molar ratio inputs were used to give the following final concentrations of radiometal and ligand (1:1 molar ratio): 1 μM (2 μM stock solutions, 1:1 buffer-to-radiometal ratio), 10 μM (40 μM stock solutions, 500:1 buffer-to-radiometal ratio), 20 μM (40 μM stock solutions, 1:1 buffer-to-radiometal ratio), 30 μM (100 μM stock solutions, 130:1 buffer-to-radiometal ratio), 50 μM (100 μM stock solutions, 1:1 buffer-to-radiometal ratio), and 90 μM (200 μM stock solutions, 11:1 buffer-to-radiometal ratio). Experiments were performed with the same settings as listed above, and with $t_{RES}$=12 minutes and at a temperature of 37° C. After the collection of product, the extent of reaction was determined as described in section 3.7.3.

Throughout the course of radiolabeling experiments, three trial runs were performed before data was recorded to ensure proper functioning of the microreactor after syringe pump or heater settings were changed and after depleted syringes were replenished.

3.7.3 Measurement of Radiolabeling Yield

At the end of each reaction run, a 1 μL aliquot of product was spotted onto a radio-TLC plate and developed using a mobile phase of methanol/10% ammonium formate buffer (2:1 volume ratio). After developing, the radio-TLC plates were then counted using the Bioscan radio-TLC scanner to quantify free and bound $^{64}Cu^{2+}$. The radiolabeling yields were calculated by dividing the area of the radioactivity peak obtained for the bound $^{64}Cu^{2+}$ by the total area of the radioactivity peaks obtained for both bound and free $^{64}Cu^{2+}$.

4 Results and Discussion 4.1 Compatibility of PDMS/Glass with $^{64}Cu^{2+}$

The experiments discussed in this section were performed to determine the compatibility of $^{64}Cu^{2+}$ with the materials comprising the microreactor. For microfluidic radiolabeling with $^{18}F$, the absorption of the radionuclide by PDMS can be a significant problem; previous work has shown that up to 95% of an amount of injected activity can be retained. To determine whether similar issues may affect radiolabeling in the current microreactor, the retention of $^{64}Cu^{2+}$ and the ability of PDMS and glass to withstand the emissions of this radionuclide were examined.

Figure 7:
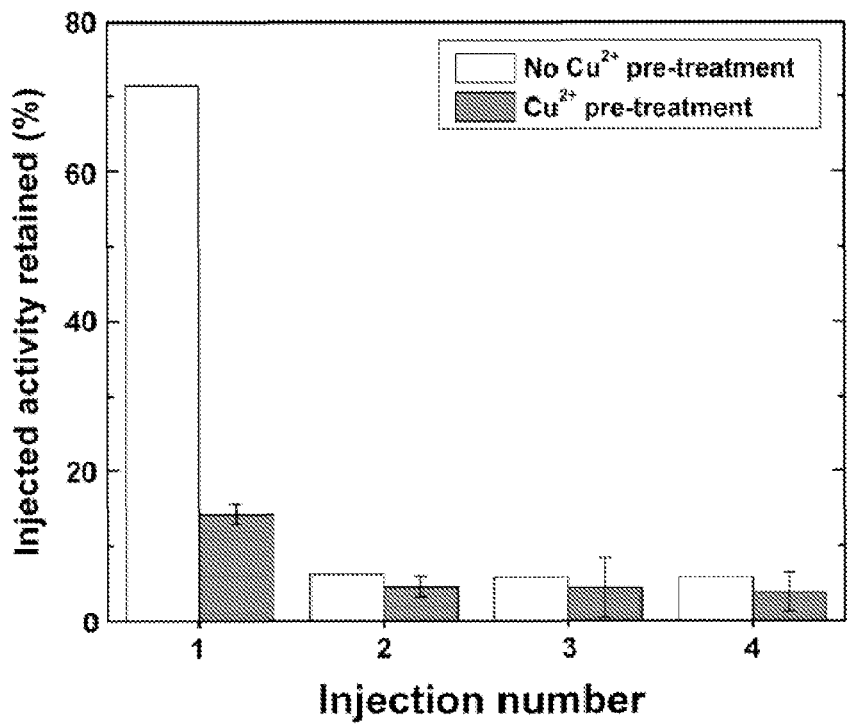
FIG. 7 shows retention of $^{64}Cu^{2+}$ in an exemplary PDMS/glass microchannel with staggered herringbone grooves. The retention measured without blocking the surface of the microchannel using non-radioactive $Cu^{2+}$ (white bars) is compared to the retention measured after blocking the surface of the microchannel using non-radioactive $Cu^{2+}$ (grey bars). Error bars represent the standard deviations of the averages of multiple experiments (n=1 for no $Cu^{2+}$ pre-treatment, n=2 for $Cu^{2+}$ pre-treatment).

FIG. 7 shows the percent of injected activity of $^{64}Cu^{2+}$ retained in a single microchannel (length~3 cm, volume~0.6 μL) with staggered herringbone grooves defined in the ceiling, for a series of injections of activity. The white bars represent data for a microchannel that has been washed with nitric acid, and the grey bars represent data for a microchannel that has been washed with nitric acid and then pre-treated with a non-radioactive $Cu^{2+}$ solution (section 3.6). The microchannel that was not pre-treated with $Cu^{2+}$ solution retained a substantial portion of the activity of the first injection (~70%), but retained only ~5% of the activity of subsequent injections. The microchannel that was pre-treated with $Cu^{2+}$ solution retained only ~15% of the activity of the first injection and also retained only ~5% of the activity of subsequent injections. The difference between the retention of the activity in the first injection in the pre-treated and non-pre-treated microchannels, and the decrease in retention of activity in subsequent injections suggest that $^{64}Cu^{2+}$ probably adheres to the walls of the microchannel, though once the surface is saturated, no further adhesion occurs. The adhesion of the $^{64}Cu^{2+}$ is presumably due to non-specific, electrostatic interactions between the positively-charged copper ions and the negatively-charged glass surface; polymer coatings with similar chemical groups to those of PDMS are used to minimize electrostatic interactions between positively-charged solutes and the surfaces of capillary electrophoresis equipment made of glass.

To confirm the hypothesis that non-specific electrostatic interactions between the microchannel surface and the $^{64}Cu^{2+}$ are responsible for the retention observed in FIG. 7, a $Na^+$ solution was used to block the surface of the microchannel. Following this pre-treatment, the inventors observed the same decrease in the percentage of injected activity retained as for the case when the microchannel was pre-treated with the $Cu^{2+}$ solution (data not shown). From this and the preceding results, the inventors conclude that the retention of $^{64}Cu^{2+}$ on the glass surface is primarily due to electrostatic interactions and not due to absorption of the ions into the PDMS. The retention of $^{64}Cu^{2+}$ in the microchannel can be minimized either by changing the charge of the glass surface of the microchannel to positive, by functionalizing the glass with a positively-charged silane, for example[25], or by fabricating the microreactor completely in PDMS. Note: in the radiolabeling experiments discussed in later sections, data for the first three reactions performed in the microreactor are ignored. This procedure ensures that the influence of $^{64}Cu^{2+}$ retention on the measured extent of reaction is minimal, by saturating the surface of the microreactor with copper ions.

Over the course of the experiments performed in this work, a single microreactor was employed. In total, the device was exposed to 260 mCi of radiation over 720 hours. Only after this exposure were signs of damage observed—the microreactor began leaking, indicating that the seal between the PDMS and glass had decayed. Thus, the device is sufficiently robust for its envisioned role as a single- or multiple-use (<20), disposable microreactor for radiolabeling.

4.2 Microfluidic Radiolabeling

In this section, the radiolabeling of DOTA-cyclo(RGDfK) with $^{64}Cu^{2+}$ using a 1:1 stoichiometric ratio of the two reagents is examined. For the purpose of evaluating the performance of the microreactor, all experiments were performed using carrier-added $^{64}Cu^{2+}$, so that the concentration of $Cu^{2+}$ was known, and to maximize the number of experiments that could be performed with one batch of the radiometal. Thus, although the disclosure refers to $^{64}Cu^{2+}$ solutions, over 99% of the copper present in the solutions is not radioactive. For the purpose of operating the microreactor in the clinic, in the production of PET imaging agents, for example, undiluted radiometal solution obtained directly from the cyclotron would be used instead.

Figure 5A:
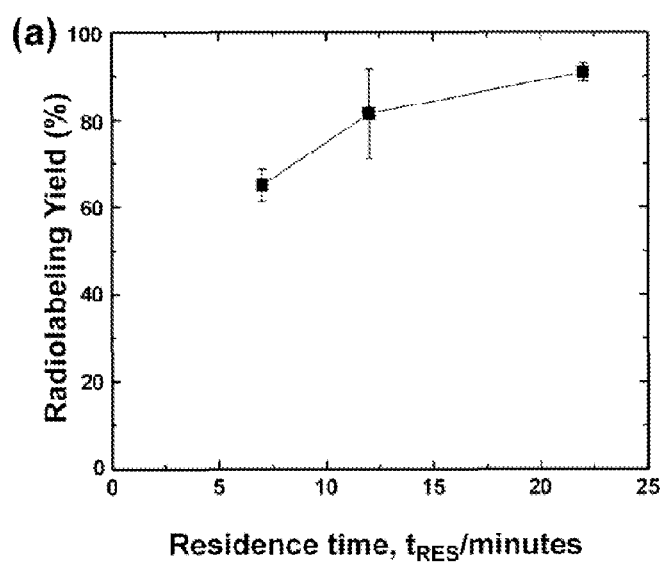
FIGS. 5(a)-5(b) show radiolabeling yield for the production of $^{64}Cu$-DOTA-cyc/o(RGDfK) as a function of (a) residence time, $t_{RES}$, and (b) radiolabeling method at various temperatures, T. In (a), error bars represent standard deviation in the extent of reaction for experiments using radiometal solutions made from the same batch of $^{64}Cu^{2+}$ for $t_{RES}=7$ and 22 minutes (n=3) and between experiments using radiometal solutions made from three different batches of $^{64}Cu^{2+}$ for $t_{RES}=12$ minutes (3 repetitions for each batch, n=9). Experiments were performed at T=37° C. Lines between points are guides for the eye. In (b), for the 'Microreactor' method, error bars represent the standard deviation in extent of reaction between three experiments using radiometal solutions made from two (T=23 and 47° C., n=6) and three (T=37° C., n=9) different batches of $^{64}Cu^{2+}$. For the other two methods, error bars represent the standard deviation in extent of reaction between three experiments using radiometal solutions made from the same batch of $^{64}Cu^{2+}$ (n=3). Experiments were performed with $t_{RES}=12$ minutes. All experiments were performed using a 1:1 stoichiometric ratio of $^{64}Cu^{2+}$ to DOTA-cyclo(RGDfK).

In FIG. 5a, the radiolabeling yield (i.e., the percent of $^{64}Cu^{2+}$ chelated by DOTA-cyclo(RGDfK)) obtained by mixing 50 μM solutions of $^{64}Cu^{2+}$ and DOTA-cyclo(RGDfK) at a 1:1 stoichiometric ratio, and incubating the mixture at 37° C. for residence times, $t_{RES}$, of 7, 12 and 22 minutes, is presented. The data indicate that, at this concentration of reagents, over 80% of the radiometal is chelated after 12 minutes. To test reproducibility, the radiolabeling yield for this residence time was measured for solutions made from three separate productions of $^{64}Cu^{2+}$. The standard deviation for this average is larger than those for experiments that were performed with the same batch of $^{64}Cu^{2+}$ (7 and 22 minutes), indicating the variability of the specific activity of the $^{64}Cu^{2+}$ between productions. This variability results in changing amounts of trace metal contaminants that can compete with $Cu^{2+}$ for chelation with DOTA (e.g., Ni, Fe, and Zn).

Figure 5B:
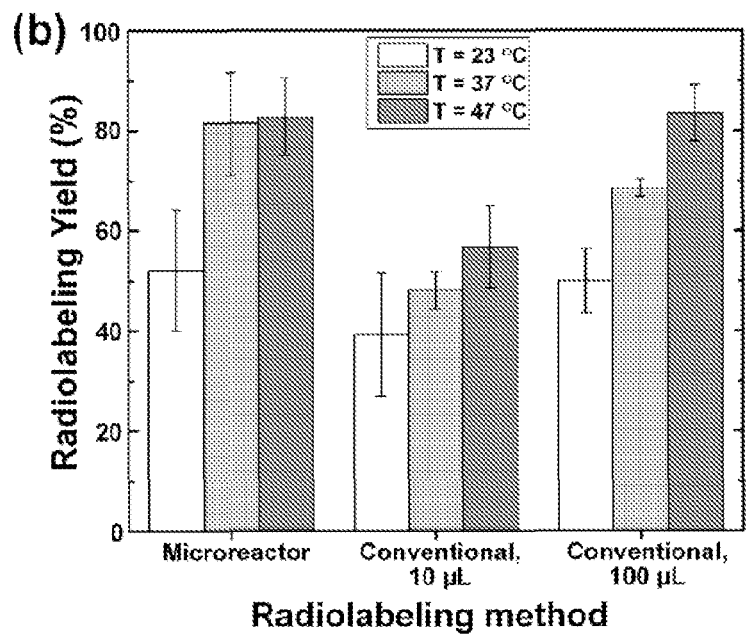

To contextualize the improvement in radiolabeling provided by the microreactor, a direct comparison is made between the radiolabeling yield obtained by the microreactor and those obtained through conventional radiolabeling methods, again using a 1:1 stoichiometric ratio of $^{64}Cu^{2+}$ to DOTA-cyclo(RGDfK). To make this comparison, a residence time of 12 minutes and a radiometal/ligand concentration of ~30 μM is chosen such that the radiolabeling yield is high enough to be measured accurately, but does not reach 100% in the microreactor, based on the results in FIG. 5a. FIG. 5b shows the radiolabeling yield for the chelation of $^{64}Cu^{2+}$ by DOTA-cyclo(RGDfK) obtained using three different radiolabeling methods at three different temperatures. 'Conventional, 10 μL' and 'Conventional, 100 μL' represent data obtained when the reaction was performed using conventional radiolabeling procedures with small volumes (~10 μL) and large volumes (~100 μL), respectively (section 3.7.1). The yields obtained using the microreactor at 37 and 47° C. were significantly higher than those obtained using the 10 μL conventional procedure. The inventors speculate that the superior mixing of small volumes of reagents achieved by the microreactor resulted in this improved performance. To support this hypothesis, the yields obtained using the microreactor were compared to those obtained using conventional procedures with a larger volume (Conventional, 100 μL), in which more efficient mixing is possible through vortexing. For both methods, the yield is the same at 23 and 47° C., within experimental error, indicating that the mixing achieved by the microreactor and by macro-scale vortexing is sufficient to overcome the diffusive mass transfer limitations to the radiolabeling reaction that hinder the performance of the 'Conventional, 10 μL' method. For the microreactor, the yield obtained at 37° C. is the same as that obtained at 47° C., within experimental error. This result suggests that the microreactor achieves the maximum yield possible for reagent concentrations of ~30 μM and $t_{RES}$=12 minutes at a lower temperature than the conventional method, and may also suggest improved performance through enhanced heat transfer in the microreactor.

In addition to enhancing reaction rates through efficient mass and heat transfer, the ability of microfluidic systems to manipulate small volumes of concentrated reagents can potentially lead to high radiolabeling yields. In FIG. 6, radiolabeling yield is plotted as a function of the final concentration of 64Cu2+, MF, (i.e., the concentration after all solutions are mixed together) for a stoichiometric ratio of 64Cu2+ to DOTA-cyclo(RGDfK) of 1: 1, $t_{RES}$=12 minutes, and an incubation temperature of 37° C. The data show that, by increasing the final concentration of the reagents to >50 μM, yields approaching >90% are obtainable with these reaction conditions. Due to the 1:1 stoichiometric ratio, the need for the separation of unlabeled BFC-BMs is eliminated once yields reach >90%. As mentioned previously, the concentration of radiometal obtained from the cyclotron is typically 1-2 mCi≈4 picomoles in ~10 μL, or ~0.4 μM. Final concentrations ≤50 μM could be obtained for the clinical production of radiopharmaceuticals by (1) minimizing the dilution of the radiometal solution by using highly concentrated solutions of buffer and ligand, and (2) implementing a microfluidic means of increasing the concentration of the radiometal, such as through the evaporation of water from the radiometal solution.

The microfluidic reactor has further been employed to (a) validate the adhesion of another radiometal, gallium-68 ($^{68}$Ga), to the reactor; (b) radiolabel two different bifunctional chelators (BFCs) with two different radiometals; (c) perform an on-chip parametric study to obtain high radiolabeling efficiencies; and (d) radiolabel a large biomolecule as a model for antibody or protein.

4.2.1. Adhesion of Gallium-68 to Microreactor

Similar to copper-64, the adhesion of gallium-68 to microreactor is investigated.

Method:

A 3 cm-long, 200 μm-wide, 100 μm-tall microchannel with staggered herringbone grooves, fabricated from poly(dimethylsiloxane) PDMS and glass and with a volume of ~0.6 μL, was used for these experiments. Prior to use, the microchannel was cleaned with 1 mL of 1N nitric acid to remove trace metals, and flushed with 3 mL of 10 mM NH$_4$OAc buffer solution.

For pre-treatment with Ga$^{3+}$/Na$^+$: 100 μL of a 10 mM GaCl$_3$/100 mM NaCl solution was injected into the microchannel and allowed to sit for 30 minutes. The microchannel was then flushed with 1 mL of 10 mM NH$_4$OAc buffer solution (pH=6.8).

For retention measurement, 30 μL of no carrier-added (only radioactive) $^{68}$Ga$^{3+}$ in 10 mM NH$_4$OAc buffer solution (pH=6.80) was injected into the microchannel. After 10 minutes, the 68Ga$^{3+}$ solution was displaced from the microchannel by 200 μL of air, via syringe. The microchannel was then flushed with 200 μL of 10 mM NH4OAc buffer. The percent of injected activity retained in the microchannel was calculated from the known activity of the injected solution, and the difference between the activity left behind in the microchannel after flushing and the initial activity of the microchannel measured before the $^{68}$Ga$^{3+}$ solution was injected, all measured with the Capintec radioisotope dose calibrator.

Results and Discussion

Figure 8:
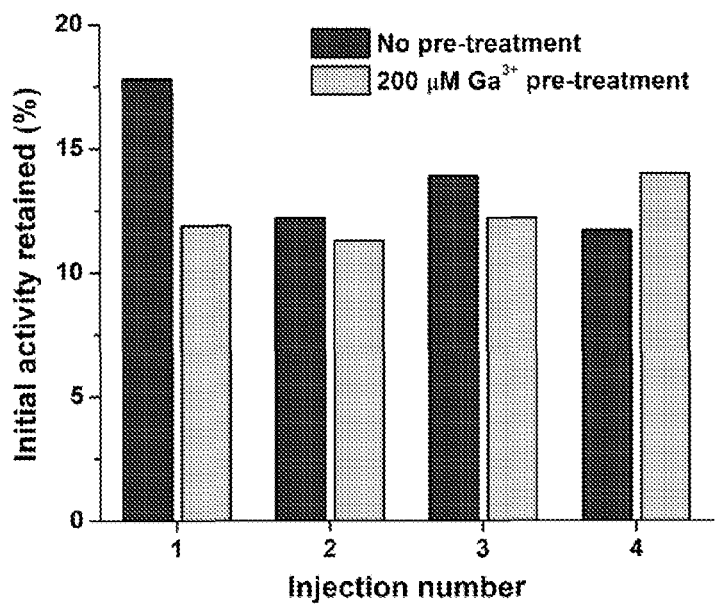
FIG. 8 shows retention of $^{68}Ga^{3+}$ in an exemplary PDMS/glass microchannel with staggered herringbone grooves. The retention measured without blocking the surface of the microchannel using non-radioactive $Ga^{3+}$ (darker bars) is compared to the retention measured after blocking the surface of the microchannel using non-radioactive $Ga^{3+}$ (paler bars).

FIG. 8 shows the percent of injected activity of $^{68}$Ga$^{3+}$ retained in a single microchannel with staggered herringbone grooves defined in the ceiling, for a series of injections of activity. The darker bars represent data for a microchannel that has been washed with nitric acid, and the paler bars represent data for a microchannel that has been washed with nitric acid and then pre-treated with a non-radioactive Ga$^{3+}$ solution. The microchannel that was not pre-treated with Ga$^{3+}$ solution retained higher activity of the first injection (~17%), but retained a lower activity (~12%) of the activity of subsequent injections. The difference between the retention of the activity in the first injection in the pre-treated and non-pre-treated microchannels, and the decrease in retention of activity in subsequent injections suggest that $^{68}$Ga$^{3+}$ probably adheres to the walls of the microchannel, though once the surface is saturated, no further adhesion occurs. The adhesion of the $^{68}$Ga$^{3+}$ is presumably due to non-specific, electrostatic interactions between the positively-charged copper ions and the negatively-charged glass surface. This adhesion behaviour is similar to copper ($^{64}$Cu$^{2+}$), though gallium adheres less than copper.

To confirm the hypothesis that non-specific electrostatic interactions between the microchannel surface and the $^{68}$Ga$^{3+}$ are responsible for the retention observed, a Na$^+$ solution was used to block the surface of the microchannel. Following this pre-treatment, a similar decrease was observed in the percentage of injected activity retained as for the case when the microchannel was pretreated with the Ga$^{3+}$ solution (data not shown). From this and the preceding results, the inventors concluded that the retention of $^{68}$Ga$^{3+}$ on the glass surface is primarily due to electrostatic interactions and not due to absorption of the ions into the PDMS.

4.2.2. Radiolabeling of Two Different BFCs with Two Different Radiometals

The versatility of our microreactor for labeling different chelators with different radiometals is demonstrated. Previously, the microreactor was used to label DOTA-RGD with copper-64, where RGD is a tumor targeting biomolecule.

Method:

The microreactor design and the procedures employed for sample preparation, conventional and microreactor-based labeling, and analysis are similar to those described previously. The radioactive gallium was procured from a gallium generator and used without further purification. The bifunctional chelators used were 1,4,7,10-tetraazacyclododecane-1, 4,7,10-tetraacetic acid (DOTA) and 1,4,7-triazacyclononane-1,4,7-triacetic acid (NOTA), and the radiometals were copper-64 and gallium-68. The biomolecule was again RGD. The concentration of copper was 50 μM, while that of gallium was 100 μM for labeling NOTA-RGD and 50 μM for DOTA-RGD. The ratio of the concentration of radiometal-to-biomolecule was 1:1. The residence time (10 minutes) and labeling temperature (37° C.) were maintained constant for all the experiments.

Figure 9A:
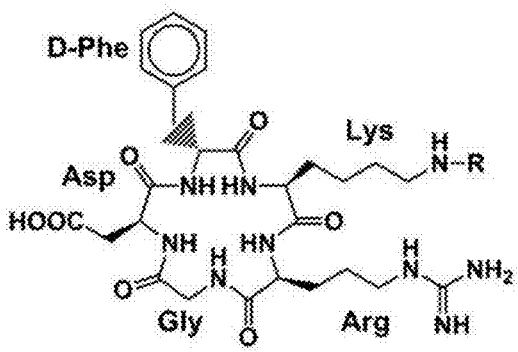
FIGS. 9(a) and 9(b) show (a) the biomolecule RGD used for imaging tumors; and (b) radiolabeling schemes tested.
Figure 9B:
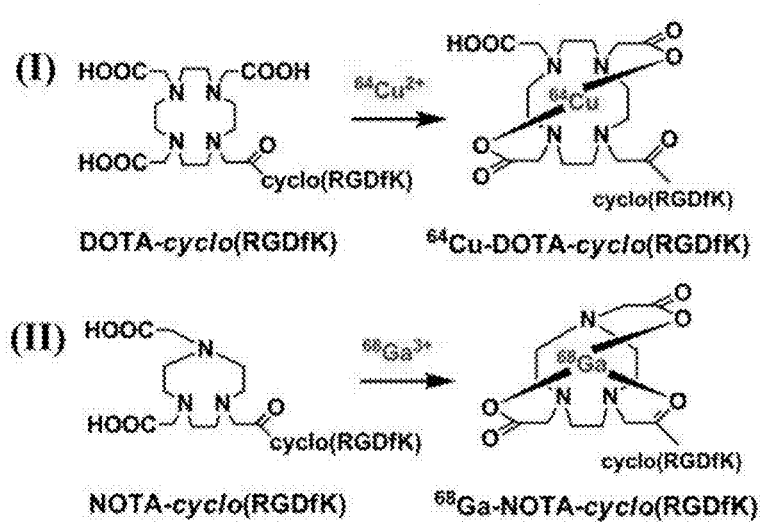

Results and Discussion:

The radiolabeling schemes for $^{64}$Cu-DOTA-RGD and $^{68}$Ga-NOTA-RGD are shown in FIG. 9 ($^{68}$Ga-DOTA-RGD is not shown).

Figure 10:
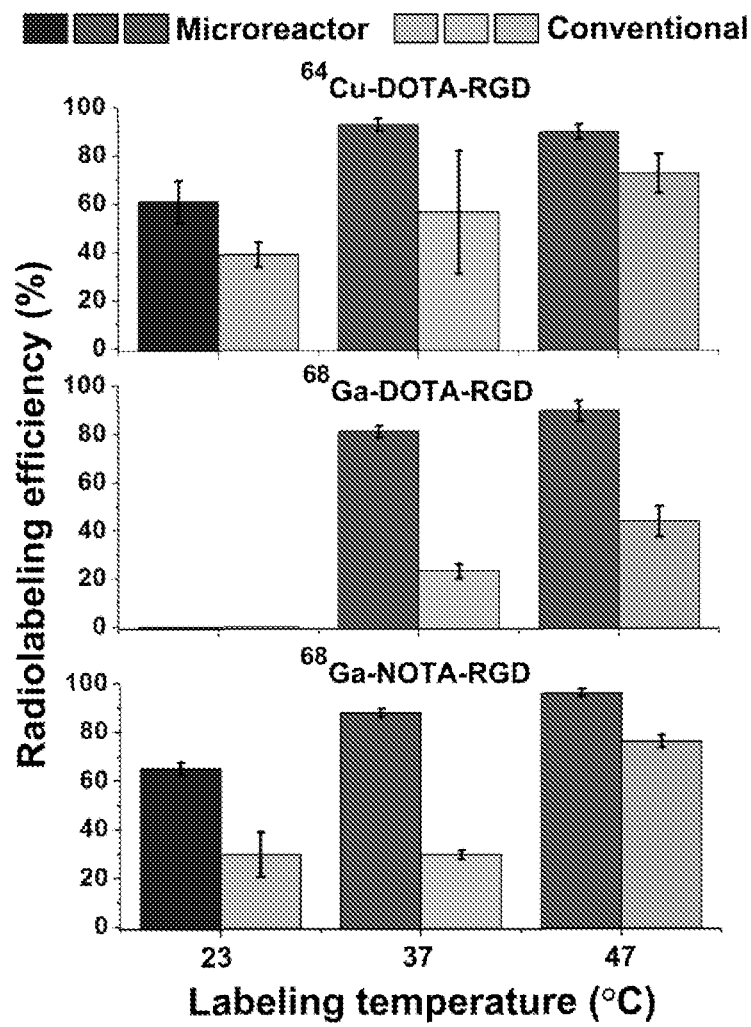
FIG. 10 shows a comparison of radiolabeling efficiencies for three different systems at three different temperatures.

The comparison of radiolabeling efficiencies for $^{64}$Cu-DOTA-RGD, $^{68}$Ga-DOTA-RGD and $^{68}$Ga-NOTA-RGD between those obtained using the microreactor and conventional procedures are shown in FIG. 10. The higher efficiencies were achieved using the microreactor due to the more effective mixing of small volumes, and enhanced heat transfer. The inventors also observed the radiolabeling to be more reliable using the microreactor, evident by the lower error bars for microreactor-based labeling. The improvement in performance of the microreactor is more evident for radiolabeling with $^{68}$Ga, as the labeling is more sensitive to temperature, and the enhanced heat transfer in the microreactor is expected to have a stronger influence on the labeling kinetics.

4.2.3. On-Chip Parametric Study for Maximizing Radiolabeling Efficiency

To demonstrate the application of the microreactor for screening reaction conditions, a parametric study was performed to maximize the radiolabeling efficiency.

Method:

The radiometal-to-biomolecule concentration ratio was maintained constant at 1:1, as in the previous radiolabeling experiments (section 2). The procedures for sample preparation, conventional and microreactor-based labeling, and analysis were also similar to those in section 2. The residence time and the concentration of radiometal were varied.

Figure 11A:
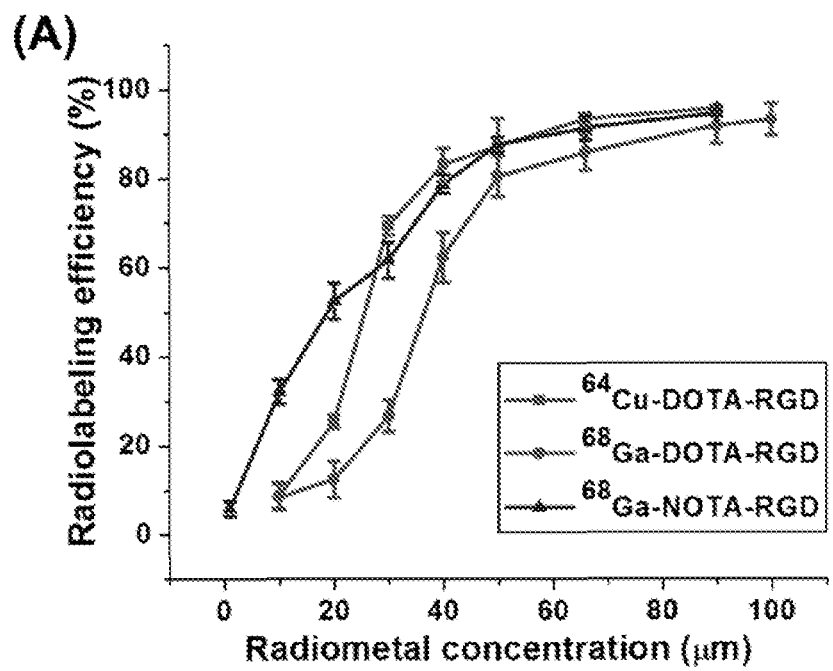
FIGS. 11(a) and 11(b) show the effect of (a) radiometal concentration and (b) reaction or residence time on radiolabeling efficiency for the three schemes; labeling was performed on-chip.
Figure 11B:
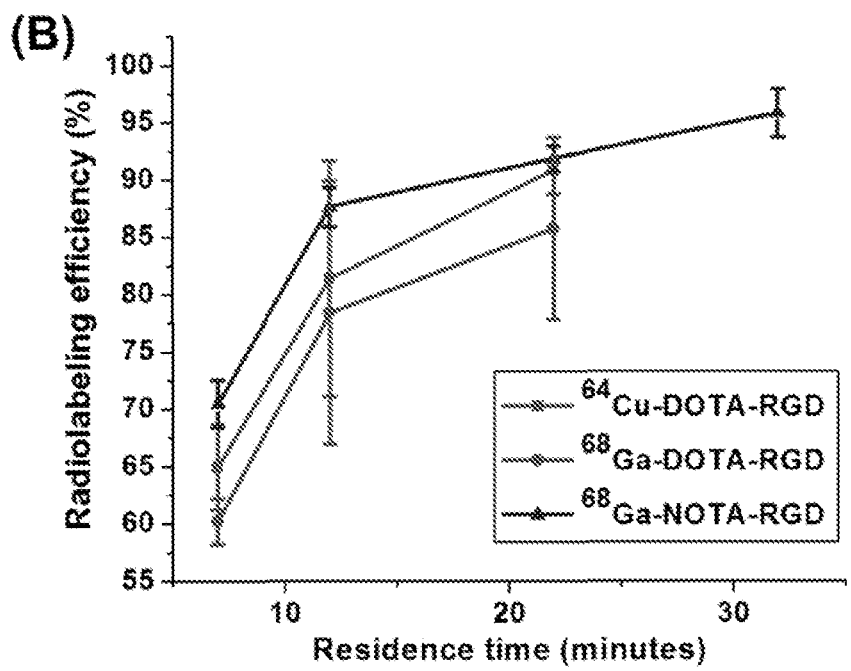

Results and Discussion:

The parametric study for labeling three different studies is shown in FIG. 11. It was observed that radiolabeling efficiencies greater than 90% could be achieved for radiometal concentrations greater than 50 µM within 20 minutes. More importantly, these high efficiencies were achieved without using excess of any reagents, thus avoiding any chromatographic purification.

4.2.4. Labeling of Large Biomolecules Using the Microreactor

In addition to RGD, the microreactor is used to label a large biomolecule, bovin serum albumin (BSA), for two reasons. Firstly, since many PET imaging agents use antibodies as targeting biomolecules, the application of the microreactor to label BSA, which serves a model for labeling proteins or antibodies, is demonstrated. Secondly, BSA is a much larger molecule compared to RGD, where the molecular weight of BSA is 66776 g/mol and that of RGD is only 603.7 g/mol. A larger molecule has a lower diffusivity, and hence, the labeling reaction maybe diffusion-limited.

Method:

For the labeling experiments, the concentrations of copper and gallium were 1 µM and 5 µM, respectively. The residence time was 20 minutes, and the labeling temperature was 37° C. The procedures for sample preparation, conventional and microreactor-based labeling, and analysis were also similar to those in section 2.

Figure 12:
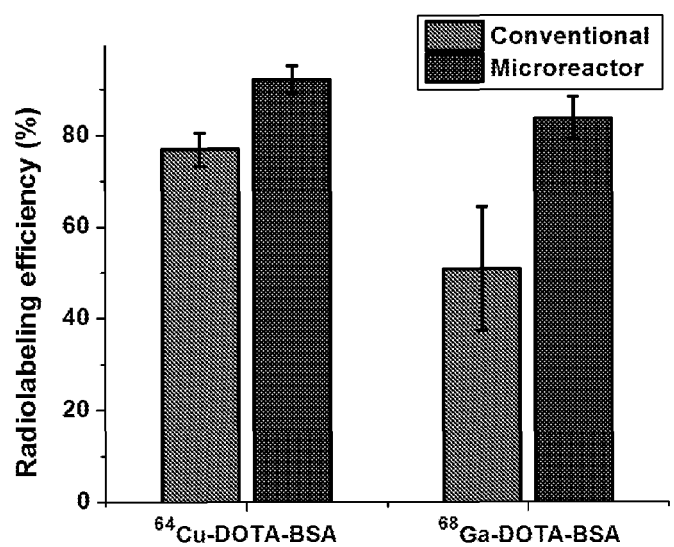
FIG. 12 provides a comparison of radiolabeling efficiencies for labeling bovine serum albumin (BSA).

Results and Discussion:

The labeling results and the comparison with conventional procedures are shown in FIG. 12. The data reveal that the labeling efficiencies are higher for the microreactor and more reliable. The high efficiencies also indicate that the labeling in the microreactor is not diffusion limited.

5 Conclusions of Radiolabeling Investigation

An exemplary microreactor made from PDMS and glass for radiolabeling biomolecule-bifunctional chelator conjugates (BFC-BMs) with radiometals for application as imaging or therapeutic agents in nuclear medicine has been described. The microreactor is able to efficiently mix small volumes of reagents (~10 µL or less) by using chaotic advection that is induced by staggered herringbone grooves defined in a mixing microchannel in which reagents are combined, and to incubate the reaction mixture at elevated temperatures after it fills several micro-reservoirs (total volume=50 µL). The performance of the microreactor was tested by radiolabeling different BFCs, DOTA and NOTA, conjugated to biomolecules of varying sizes, RGD and BSA, with two different radiometals, $^{64}$Cu$^{2+}$ and $^{68}$Ga$^{3+}$, demonstrating the versatility of the system for labeling. The materials from which the microreactor is made withstood substantial doses of radiation (260 mCi), and interacted minimally with the radiometal, once the negatively-charged glass surface of the microreactor is blocked with positively-charged ions (~5% retention of injected activity). Furthermore, from a comparison between the radiolabeling yields of the microreactor and of two conventional radiolabeling methods at various temperatures, the inventors concluded that the higher radiolabeling yield observed for the microreactor was achieved through efficient mixing with chaotic advection and through enhanced heat transfer. Finally, it was demonstrated that, by using small volumes of concentrated radiometal (~50 µM), it is possible to achieve high radiolabeling yields (>90%) without resorting to using an excess of BFC-BM to accelerate the rate of reaction, as is necessary in macro-scale, conventional radiolabeling procedures that require dilution of the radiometal. High yields with a 1:1 stoichiometric ratio of radiometal to BFC-BM eliminate the need for chromatographic purification of the product to remove unlabeled BFC-BMs, resulting in shorter synthesis times and therefore a higher specific activity of the resulting imaging or therapeutic agent. The results described here suggest that this microreactor-based approach has great potential for improving the preparation of radiopharmaceuticals in the clinic.

The chelation conditions may be further optimized for radiolabeling with other radiometals, such as $^{99m}$Tc, and to integrate pre-concentration and purification elements in the microreactor to ensure that high radiolabeling yields are obtained reproducibly, and that the radiometal solution is sufficiently pure and concentrated for the eventual clinical application of the resulting radiopharmaceuticals in humans. Furthermore, a complementary microreactor may be developed for the conjugation of bifunctional chelators to disease-specific biomolecules. Such a system would provide great versatility for the production of patient-tailored doses of imaging and therapeutic agents for nuclear medicine.

In summary, benefits of the technology include:

Efficient, passive mixing using staggered herringbone grooves and fast heat transfer across the small height of the microreactor improve reaction yields over those obtained by conventional synthesis methods;

Ability to handle a range of meso-scale volumes (1 to 50 microliters) provides the following advantages: (a) negates requirement for dilution of the radiometal, allowing high reaction rates to be attained at a 1:1 stoichiometric ratio of radio metal to ligand, which in turn negates the requirement for subsequent chromatographic purification steps; (b) allows for the production of clinically relevant quantities of imaging agents with low solubility in aqueous media, such as those incorporating antibodies;

Conjugation of BFC to BM and chelation of radio metals by BFC-BM conjugate (radiolabeling) is performed in aqueous media at near-physiological temperature and neutral pH, which allows targeting molecules such as antibodies to be labeled, since no solvents that would denature the biomolecule are required, in contrast to radiolabeling with non-metallic radionuclides, such as $^{18}$F and $^{11}$C;

Versatility of the system to label different radiolabeled complexes; and

Automated operation, the simplicity of microreactor design and its modular nature, the low cost of materials, fabrication, and ancillary equipment, and the reduced size and shielding requirements, in comparison to currently available automated synthesis modules, all contribute toward minimizing costs. The lowered cost is especially useful in a clinical environment where disposability is a key desired feature.

Altogether, these benefits may allow for the point-of-care synthesis of custom-designed PET/SPECT imaging agents in the clinic.

6 Microfluidic Conjugation of Bi-Functional Chelators to Biomolecules

Microfluidic technologies may have application to the synthesis of chemicals, from simple one-step processes to complex multi-step processes. Click chemistry is emerging as a powerful tool for the conjugation of various functional molecules, including bi-functional chelators, to biomolecules. Using a microfluidic platform to perform the click chemistry-based synthesis of multimodal imaging agents may provide additional benefits, such as versatility (through the ability to attach a variety of chelators to targeting biomolecules), low consumption of potentially expensive and hard-to-obtain reagents, faster synthesis times, and better synthetic reproducibility through automation. This technology has the following beneficial features:

- Integration of conjugation chemistries on the same platform using a click chemistry-based approach;
- Ability to handle small volumes of reagents (as low as 1 μL), which may avoid the need for dilution of the reagents for the conjugation reaction, and subsequently lead to high conjugation reaction rates for a 1:1 stoichiometry;
- Precise control over reagent volumes and concentrations, which may ensure that the reagents are combined in the desired stoichiometric ratios, and hence, avoid the purification steps typically required when one of the reagents is used in excess;
- Integration of heating and incubation on the same microfluidic platform, which may result in reduced loss of reagents during transfer between different processes, faster rates of heat transfer, and smaller overall system size;
- Ability to perform conjugation reactions using aqueous chemistries, which is preferred over labeling in organic solvents for biomolecules such as antibodies and other proteins;
- A re-useable, surface-immobilized $Cu^{1+}$ catalyst for click chemistries—the high surface area to volume ratio of microchannels may be a benefit for the heterogeneous catalysis of conjugation reactions; and
- High degree of automation.

Figure 13:
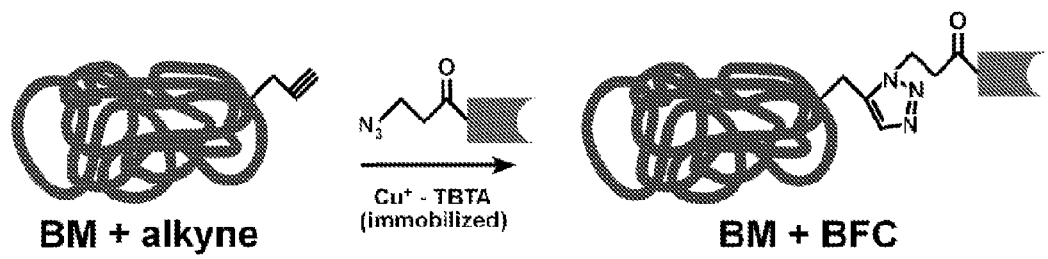
FIG. 13 shows a Cu(I)-catalyzed azide-alkyne [3+2] cycloaddition reaction used to conjugate targeting biomolecules (BM) with bi-functional chelators (BFC). The Cu(I) is immobilized to the surface of the microreactor using Tris-[(1-benzyl-1H-1,2,3-triazol-4-yl)methyl]amine (TBTA).

The click reaction relied on exclusively for performing the conjugation of BFCs to BMs is shown in FIG. 13: the copper (I)-catalyzed azide-alkyne [3+2] cycloaddition reaction. The order and choice of the reaction scheme and reaction conditions for this scheme may be optimized to result in shorter synthesis time, higher reaction yield, and higher purity.

Figure 14:
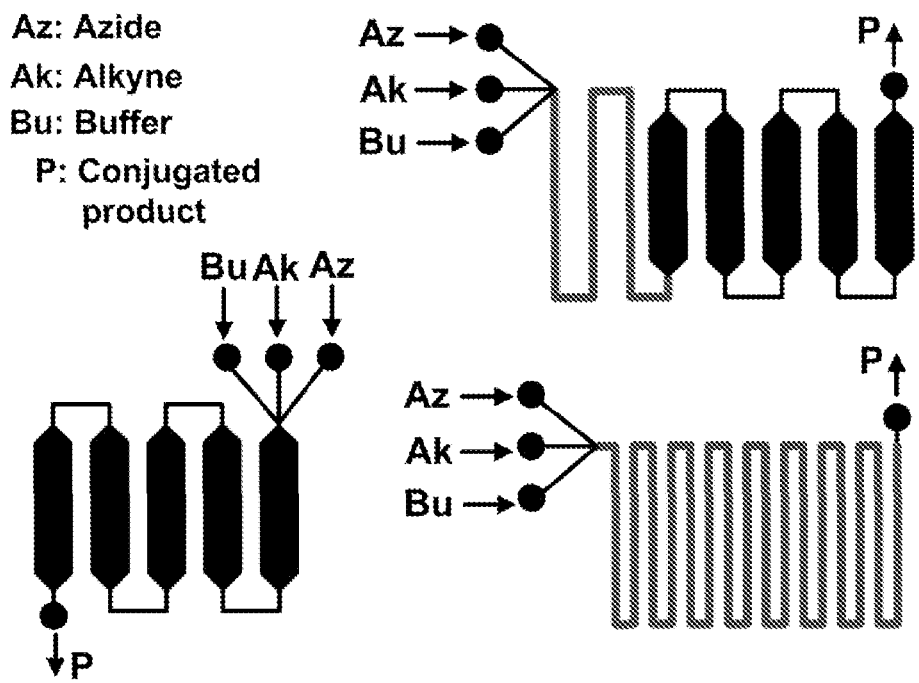
FIG. 14 provides an illustration of different designs for an exemplary conjugation microreactor. The thicker lines indicate microchannels with staggered herringbone grooves on one surface. Cu(I) catalyst is immobilized on all surfaces.

An illustration of the various microreactor designs used to conjugate BFCs to biomolecules is shown in FIG. 14. The microreactor may be built from PDMS and glass, as before, and may include a set of microchannels with dimensions to the microchannels of the radiolabeling microreactor. Each of the microchannels may contain staggered herringbone grooves to generate chaotic advection; this advection may assist in transporting the BM and BFC reagents to a Cu(I) catalyst immobilized on the microchannel surfaces.

The microreactor has been used to perform a click-reaction using copper (I) as a catalyst. A protocol has been developed for immobilizing copper (I) on glass surfaces, and the protocol has been used for immobilizing copper (I) on microreactor channel walls.

6.1.1. On-Chip via Copper (I)-Assisted Click Chemistry

The inventors have hypothesized that efficient mixing and enhanced heat transfer in microchannel will lead to higher reaction efficiencies in the microreactor.

Method:

A microreactor design that is identical to the one used for previously reported radiolabeling experiments was employed in the following experiments. A Flu-568 azide (100 μM) was mixed with Propargylamine (100 μM), and the azide-alkyne mixture was reacted with copper (I) as a catalyst. The copper (I) was synthesized by in situ reduction of copper sulfate (1 mM) with sodium ascorbate (10 mM). The solution was mixed in the serpentine herringbone channel network of the microreactor and incubated in the reservoirs at 37° C. for different residence times. The click product was analyzed using fluorescence.

Results and Discussion

Figure 15:
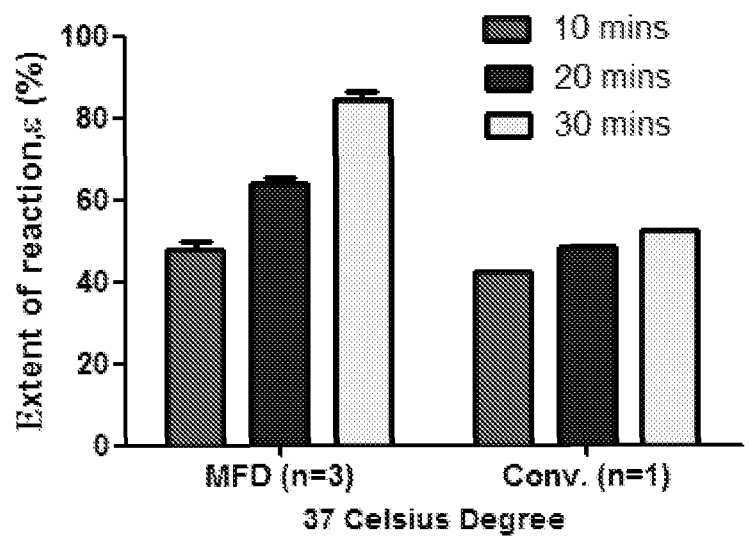
FIG. 15 provides a comparison of click reaction efficiencies for a conventional reactor and the microreactor as a function of residence time.

The comparison of click reaction efficiencies as a function of residence time obtained using the microreactor and conventional procedures are shown in FIG. 15. The higher efficiencies were achieved using the microreactor due to the more effective mixing of small volumes, and enhanced heat transfer.

6.2. Protocol for Immobilizing Copper (I) on Glass

Although the efficiencies of the click reactions were high in the microreactor (~80%), even higher values can be achieved by immobilizing the catalyst (copper (I)) on the channel walls. Since the surface-to-volume ratio is higher at the microscale, more of the solute molecules will be in contact with the catalyst, thus enhancing the reaction efficiencies. Additionally, the use of immobilized catalyst avoids the need for removing the catalyst from the click product.

Method:

An exemplary procedure for immobilizing copper (I) on glass is as follows:

Clean the glass surface: Corning glass microscope slides were sonicated for 10 minutes in 250 mL of 95% acetone & 5% Milli-Q $H_2O$. Then, the slides were sonicated for 5 minutes in 250 mL Milli-Q H2O, and these two steps were repeated twice. Finally, the slides were air-dried in a purifier vertical clean bench.

Attach silane acrylate to the glass: To each slide, 2 silicon isolators were attached (Grace Bio-labs; JTR20R-2.0; 20 mm dia.×2 mm depth), forming 2 wells on the glass slide. Then, TMSPA (3-(Trimethoxysilyl)propyl acrylate, Aldrich cat#475149) was attached to the glass surface. After filling the wells with TMSPA, they were incubated for 1 hour at 37° C., and then washed thoroughly with acetone.

Attach copper (I) stabilizing molecule to silane: Since copper (I) has the tendency to oxidize readily to copper (II), tris[(1-benzyl-1H-1,2,3-triazol-4-yl)methyl]amine or TBTA was used to stabilize copper (I). To each well, 10 mM TBTA derivative dissolved in methanol was added, and then the silane attachment was initiated by adding 30 μL Borax aqueous solution. The reaction mixture was incubated overnight at room temperature in the purifier vertical clean bench. Then, the wells were washed thoroughly with acetone and Milli-Q $H_2O$.

Immobilize copper (I): 200 μL Cu(I) stock solution (prepared by mixing 0.9 mL 100 mM sodium ascorbate with 3.6 mL 10 mM CuSO4), was added to the pre-treated wells, and then shaken for 30 minutes at room temperature. Finally, the wells were washed thoroughly with Milli-Q $H_2O$.

Since copper-64 was used, the amount of immobilized copper was quantified by measuring the radiation count. For control, copper (I) was also immobilized on non-treated glass surfaces.

Results and Discussion

The amount of copper (I) immobilized per unit area was observed to be 267 μmoles/m².

6.3. Protocol for Immobilizing Copper (I) on Channel Walls of the Microreactor

The above protocol was adapted to immobilize copper (I) in intact microfluidic channels.

Method:

An exemplary protocol for immobilizing copper (I) on microchannel walls is as follows:

Flush the microchannels with isopropyl alcohol (IPA) and remove any bubbles present.

Fill the channels with $H_2O:H_2O_2:HCl$ (5:1:1) solution at 10 μL/min, and let the solution sit in the channels for 10 minutes, Flush the channels with water to remove any trace of solution in previous step and then $N_2$ gas to completely dry out the microchannels.

Flow TMSPA (silane) and let it sit in the channel for 30 minutes, room temperature. After filling in the silane, remove the outlet tubing, and completely cover the device with crystal clear tape.

Flush the channels with isopropyl alcohol, then with $N_2$.

Prepare stock solution of 10 mM PEG-TBTA in 5% (by volume) Borax solution in water. Mix small amount of PEG-TBTA with Borax at 10:1 volumetric ratio. Use approximately 300 μL of the PEG-TBTA solution and 30 μL of Borax. Flow the solution through the channels and let it sit for at least 24 hours. To minimize water evaporation, either cover the device completely with crystal clear tape or place the device in an almost 100% relative humidity environment.

Flush the channels with IPA+water.

Mix 0.9 mL 100 mM sodium ascorbate with 3.6 mL 1 mM copper sulfate. Flow this solution through the channels and let it sit for 30 minutes.

Flush with water, and then blow out the water with nitrogen.

Results and Discussion

The amount of copper (I) immobilized per unit area was observed to be 43-52 μmoles/m², which is approximately 5 times lower than that observed for conventional immobilization protocols. The inventors speculate that the interaction of the reagent molecules with the channel walls, especially due to extended exposure under no flow, results in lower immobilization efficiencies. These issues may be addressed by modifying the above protocol to continuously stir the reagent solutions during the various immobilization steps, or use a different material for the channel walls.

Although the present invention has been described in considerable detail with reference to certain embodiments thereof, other embodiments are possible without departing from the present invention. The spirit and scope of the appended claims should not be limited, therefore, to the description of the preferred embodiments included here. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

What is claimed is:

1. A method of preparing a radiolabeled complex, the method comprising:

flowing a precursor radiometal solution comprising a metallic radionuclide through an upstream mixing portion of a microchannel, the upstream mixing portion including one or more passive mixing elements, and the metallic radionuclide being selected from $^{60}Cu^{2+}$, $Cu^{61}Cu^{2+}$, $^{64}Cu^{2+}$, $^{67}Cu^{2+}$, $^{66}Ga^{3+}$, $^{67}Ga^{3+}$, and $^{68}Ga^{3+}$;

flowing a buffer solution through the upstream mixing portion;

passively mixing the buffer solution and the precursor radiometal solution while in the upstream mixing portion to form a radiometal solution comprising the metallic radionuclide, the radiometal solution further flowing through a downstream mixing portion of the microchannel, the downstream mixing portion including one or more passive mixing elements and being disposed downstream of the upstream mixing portion;

flowing a ligand solution comprising a bifunctional chelator through the downstream mixing portion, the bifunctional chelator being selected from DOTA and NOTA;

passively mixing the ligand solution and the radiometal solution while in the downstream mixing portion to form a mixed solution and to initiate a chelation reaction between the metallic radionuclide and the bifunctional chelator, a molar ratio of the metallic radionuclide to the bifunctional chelator being about 1:1, and the mixed solution comprising a concentration of >50 μm of the metallic radionuclide; and completing the chelation reaction to form a radiolabeled complex, wherein completing the chelation reaction comprises halting the flow of each solution and incubating the mixed solution for a residence time of at least 12 minutes, the incubation being carried out at a temperature of at least 37° C. in at least one microfluidic reservoir in fluid communication with the microchannel and disposed downstream of the downstream mixing portion, and wherein the radiolabeled complex is obtained at a yield of at least about 80%.

2. The method of claim 1, further comprising flowing a fluid into the microfluidic reservoir after the incubation to force the mixed solution through a reservoir outlet.

3. The method of claim 1, wherein the flowing of each of the solutions occurs at a flow rate between about 0.1 μL/min and about 5 mL/min.

4. The method of claim 1, wherein the bifunctional chelator is conjugated to a targeting biomolecule.

5. The method of claim 1, further comprising:

flowing a chelator solution through a mixing portion of a second microchannel, the mixing portion including one or more passive mixing elements;

flowing a biomolecule solution through the mixing portion of the second microchannel;

passively mixing the chelator solution and the biomolecule solution to form a combined solution via a conjugation reaction; and forming the ligand solution from the combined solution.

6. The method of claim 1, wherein the width of the microchannel is between about 5 microns and about 500 microns.

* * * * *